US012740886B1

(12) United States Patent
Luo

(10) Patent No.: US 12,740,886 B1
(45) Date of Patent: Sep. 22, 2026

(54) ADJUSTABLE NASAL DILATOR DEVICE

(71) Applicant: DCSTAR INC, New York, NY (US)

(72) Inventor: David Luo, New York, NY (US)

(73) Assignee: DCSTAR INC, New York, NY (US)

( * ) Notice: Subject to any disclaimer, the term of this patent is extended or adjusted under 35 U.S.C. 154(b) by 0 days.

(21) Appl. No.: 19/375,910

(22) Filed: Oct. 31, 2025

(51) Int. Cl.
*A61F 5/08* (2006.01)

(52) U.S. Cl.
CPC .................................... *A61F 5/08* (2013.01)

(58) Field of Classification Search
CPC .......... A61F 5/08; A61F 5/56; A61F 5/05891; A61F 2250/0006
See application file for complete search history.

(56) References Cited

U.S. PATENT DOCUMENTS 6,470,883 B1 * 10/2002 Beaudry ............. A61F 13/0246 128/207.18
2002/0000227 A1 * 1/2002 Duyke ..................... A61F 5/08 606/199
2017/0290580 A1 * 10/2017 Soltanian ........... A61B 17/0401
2018/0104085 A1 * 4/2018 Castillo .................. A61F 9/026

* cited by examiner

*Primary Examiner* — Diane D Yabut
(74) *Attorney, Agent, or Firm* — HSML P.C.

(57) ABSTRACT

An adjustable nasal dilator designed to fit on a patient's nose and apply an outward expansion force to enhance airflow through the nasal passages. The device includes a supporting member, a fitting assembly, and an adjusting assembly. The supporting member has at least two opposing ends configured to laterally fit against both sides of the patient's nose. The fitting assembly includes first connecting portions attached to the nose and second connecting portions attached to the two ends of the supporting member, which mutual engage during use. The adjusting assembly allows the user to independently control the expansion level of the device, representing a major innovation over existing products. Through its adjusting mechanism, the adjusting assembly regulates a tensioning member to vary the angle of the left and right ends of the supporting member.

24 Claims, 16 Drawing Sheets

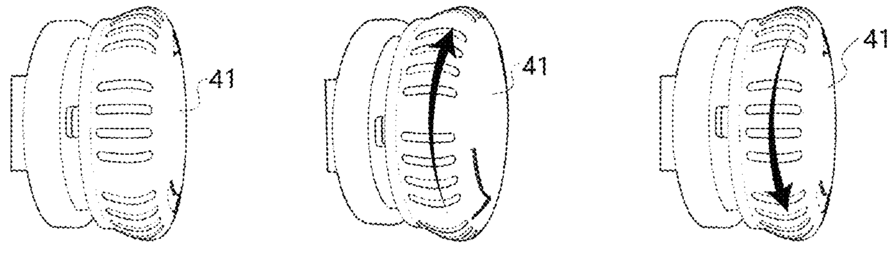
FIG. 15
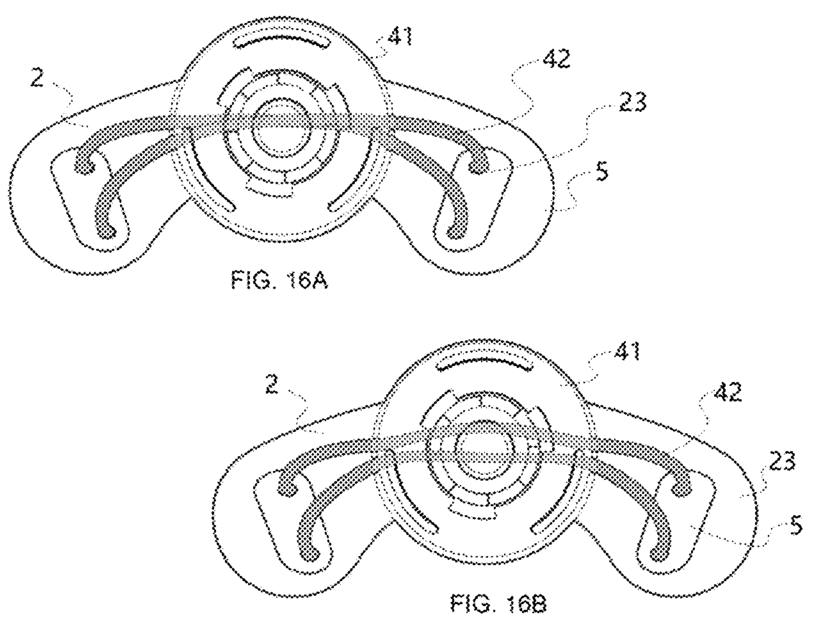
FIG. 16A
FIG. 16B

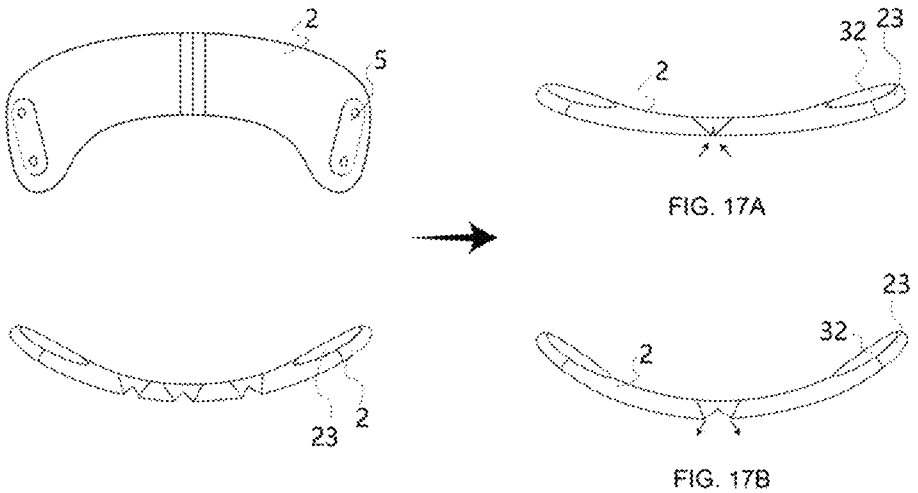
FIG. 17A
FIG. 17B
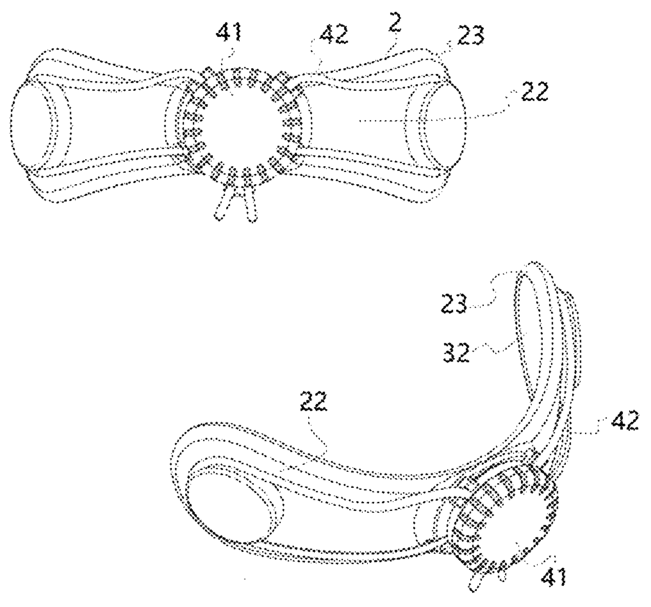
FIG. 18

ADJUSTABLE NASAL DILATOR DEVICE

TECHNICAL FIELD

The present disclosure relates to the field of respiratory assist devices, and more specifically, to an adjustable nasal dilator device. The device is configured to conform to the patient's nose and apply an outward expanding force to the nasal region, thereby enhancing the patient's breathing capacity through the nasal airway. Compared to conventional nasal dilator devices, this nasal dilator device provides an adjustable assembly that allows the patient to adjust the magnitude of the expansion force and the angles of both ends according to individual nasal morphology, ventilation requirements, and comfort preferences, achieving a personalized support effect.

BACKGROUND

In modern society, with the acceleration of daily life and increasing work pressure, people are increasingly aware of the importance of high-quality sleep for health and overall well-being. However, the majority of the population faces various respiratory-related health issues, particularly disorders associated with nasal airway ventilation. These issues not only lead to phenomena such as snoring, sleep apnea, and mouth breathing during sleep, directly disrupting sleep quality, but also may further contribute to chronic hypoxia, hypertension, cardiovascular diseases, and cognitive decline. Additionally, impaired nasal ventilation significantly reduces daytime energy and concentration, increases fatigue and anxiety, and negatively affects work efficiency and overall quality of life. With the intensification of environmental pollution, an increase in allergens, rising life pressures, and the trend of population aging, the incidence of respiratory health problems continues to rise, leading to growing attention on improving nasal function and maintaining airway health. The demand for related treatments and assistive devices is also rapidly increasing.

The causes of nasal airway ventilation disorders can generally be divided into two categories: structural abnormalities and functional diseases. Structural abnormalities, such as deviated septum, hypertrophy of the inferior turbinate, and nasal polyps, directly narrow the nasal passages and obstruct airflow. Functional diseases, including chronic rhinitis, allergic rhinitis, and sinusitis, lead to mucosal swelling and increased secretions, further affecting nasal airway patency. In addition to disease-related factors, environmental pollution, elevated airborne allergen levels, long-term unhealthy habits, and population aging contribute to the increasing incidence and severity of respiratory disorders. The combination of these multiple factors has made nasal airway ventilation dysfunction a core issue affecting respiratory health and overall quality of life in modern society.

An increasing number of people are paying attention to improving their sleep environment and respiratory health, seeking scientific sleep-assist methods and devices to enhance sleep quality. However, existing nasal dilator devices still present certain limitations, particularly with respect to structural design and adjustability. In terms of structural design, many products lack adaptability to individual differences and the complex anatomy of the nasal cavity, often resulting in insufficient fit, limited sealing, and reduced comfort. In terms of adjustment, devices usually provide only a single or limited expansion force, failing to meet the diverse needs of patients in different situations, such as changes in sleep posture or recurrent nasal inflammation. Furthermore, in terms of material selection, many dilators exhibit inadequate flexibility, limited durability, or discomfort during long-term use. In addition, some devices have a bulky appearance, which may cause a sense of foreign body or aesthetic rejection, thereby affecting patient compliance and long-term effectiveness.

There is therefore an urgent need for a novel nasal dilator device that achieves comprehensive optimization in structural adaptability, adjustment flexibility, wearing comfort, and long-term durability, in order to better meet the growing respiratory health demands in modern society.

SUMMARY

This disclosure addresses the above-described needs by providing an adjustable nasal dilator device. The device is configured to conform to the patient's nose and apply an outward expanding force to the nasal region, thereby enhancing the patient's breathing capacity through the nasal airway. The structural design improves the operational flexibility of the nasal dilator device and effectively enhances its adaptability and stability during practical use, resulting in an improved overall user experience and higher treatment compliance. The device represents a significant technical advancement with potential for widespread application.

Based on the above deficiencies, this disclosure provides a nasal dilator device that enhances operational flexibility, improves structural stability, and enhances overall effectiveness during use.

The present disclosure provides an adjustable nasal dilator device configured to conform to a patient's nose and apply an expansion force to a nasal cavity region to enhance the patient's breathing capacity through a nasal airway. The device includes:

A supporting member has a first side facing the patient's face and a second side opposite the patient's face during use. The supporting member further has at least two end portions arranged opposite to each other and configured to laterally conform to the patient's nasal sides during use.

The supporting member has a tendency for the left and right ends to extend downward.

A fitting assembly has at least two first connecting portions attached to the patient's nose during use, and at least two second connecting portions at least partially connected to the left and right ends of the supporting member. The fitting assembly is configured to mutually engage during use.

An adjusting assembly has at least one adjusting mechanism and at least one tensioning member. The adjusting assembly is configured to engage with the supporting member and, during use, adjust an angle of the left and right ends of the supporting member via the tensioning member controlled by the adjusting mechanism.

The adjusting assembly engages with the supporting member via a fixing structure that is at least provided at the left and right ends of the supporting member.

The adjusting mechanism is configured for incremental adjustment.

In an embodiment, the supporting member is at least partially made of an elastic material.

In an embodiment, the adjusting mechanism has at least a first mechanism configured to tension the tensioning member and a second mechanism configured to release the tensioning member.

In an embodiment, the first mechanism is configured to apply force in a first direction to tension the tensioning member, and the second mechanism is configured to apply force in a second direction to release the tensioning member.

In an embodiment, the first direction and the second direction are perpendicular to each other.

In an embodiment, the first direction and the second direction are completely opposite or at least partially opposite.

The present disclosure provides another adjustable nasal dilator device configured to conform to a patient's nose and apply an expansion force to a nasal cavity region to enhance the patient's breathing capacity through a nasal airway. The device includes:

A supporting member has a first side facing the patient's face during use and a second side opposite the patient's face. The supporting member further has at least two end portions arranged opposite to each other and configured to laterally conform to the patient's nasal sides during use.

The supporting member has a tendency for the left and right ends to extend downward.

A fitting assembly has at least two first connecting portions attached to the patient's nose during use, and at least two second connecting portions at least partially connected to the left and right ends of the supporting member. The fitting assembly is configured to mutually engage during use.

An adjusting assembly has at least one adjusting mechanism and at least one tensioning member. The adjusting assembly is configured to engage with the supporting member and, during use, adjust an angle of the left and right ends of the supporting member via the tensioning member controlled by the adjusting mechanism.

The adjusting assembly engages with the supporting member via a fixing structure, which is at least provided at the left and right ends of the supporting member.

The adjusting mechanism is configured to be fixed after adjustment.

In an embodiment, the supporting member is at least partially made of an elastic material.

In an embodiment, the adjusting mechanism is a knob structure.

In an embodiment, where the adjusting mechanism is a knob structure, the adjusting mechanism includes at least a ratchet wheel, a housing, a fastening member, a rotary disc, and a bottom member.

In an embodiment, the adjusting mechanism is configured such that the ratchet wheel is coupled with the housing, the fastening member and the rotary disc are integrated, and the housing is connected to the bottom member.

In an embodiment, the adjusting mechanism is a knob structure, and the tensioning member is arranged in parallel within the adjusting mechanism.

In an embodiment, the adjusting mechanism is a knob structure, and the tensioning member is arranged in a crossed configuration within the adjusting mechanism.

The present disclosure provides yet another adjustable nasal dilator device configured to conform to a patient's nose and apply an expansion force to a nasal cavity region to enhance the patient's breathing capacity through a nasal airway. The device includes:

A supporting member has a first side facing the patient's face during use and a second side opposite the patient's face. The supporting member further has at least two end portions arranged opposite to each other and configured to laterally conform to the patient's nasal sides during use.

The supporting member has a tendency for the left and right ends to extend downward.

A fitting assembly has at least two first connecting portions attached to the patient's nose during use, and at least two second connecting portions at least partially connected to the left and right ends of the supporting member. The fitting assembly is configured to mutually engage during use.

An adjusting assembly that has at least one adjusting mechanism and at least one tensioning member. The adjusting assembly is configured to engage with the supporting member and, during use, adjust an angle of the left and right ends of the supporting member via the tensioning member controlled by the adjusting mechanism.

The adjusting mechanism includes at least a first mechanism configured to tension the tensioning member and a second mechanism configured to release the tensioning member.

The adjusting assembly engages with the supporting member via a fixing structure, which is at least provided at the left and right ends of the supporting member.

In an embodiment, the supporting member is at least partially made of an elastic material.

In an embodiment, the fixing structure is further provided at a middle portion of the left and right ends of the supporting member.

In an embodiment, the fixing structure is integrally formed with the supporting member.

In an embodiment, the fixing structure and the supporting member are two separate components, which are engaged during use via at least one of a physical connection or a chemical connection.

The present disclosure provides yet another adjustable nasal dilator device configured to conform to a patient's nose and apply an expansion force to a nasal cavity region to enhance the patient's breathing capacity through a nasal airway. The device includes:

A supporting member that has a first side facing the patient's face during use and a second side opposite the patient's face. The supporting member further has at least two end portions arranged opposite to each other and configured to laterally conform to the patient's nasal sides during use.

The supporting member is at least partially made of an elastic material and has a tendency for the left and right ends to extend downward.

A fitting assembly that has at least two first connecting portions attached to the patient's nose during use, and at least two second connecting portions at least partially connected to the left and right ends of the supporting member. The fitting assembly is configured to mutually engage during use.

An adjusting assembly that has at least one adjusting mechanism and at least one tensioning member. The adjusting assembly is configured to engage with the supporting member and, during use, adjust an angle of the left and right ends of the supporting member via the tensioning member controlled by the adjusting mechanism.

The adjusting assembly is configured such that a force applied to the adjusting mechanism drives the tensioning member and transmits the force to the left and right ends of the supporting member, thereby causing at least a portion of the left and right ends to lift toward the second side.

The tensioning member has a length greater than its width.

In an embodiment, the supporting member further includes a middle section connecting the two end portions.

In an embodiment, where the supporting member has a middle section, the middle section and the two end portions are integrally formed.

In an embodiment, where the supporting member has a middle section, the middle section structure and the two end portions are two separate components.

In an embodiment, a thickness of the supporting member ranges from 0.1 mm to 20 mm.

In an embodiment, the fitting assembly is engaged with the supporting member by at least one of a snap-fit connection, adhesive connection, magnetic connection, threaded connection, or hook-and-loop connection.

The nasal dilator device of this disclosure provides at least the following beneficial effects:

1. The adjustable nasal dilator device of this disclosure represents a pioneering device in the current market with autonomous adjustment functionality, filling the technological gap of existing products in the field of adjustable nasal dilators. The device employs innovative structural design and adjusting mechanisms, overcoming long-standing technical limitations of conventional nasal dilator devices in terms of adaptability, comfort, and adjustment flexibility, and achieves personalized expansion effects for different nasal anatomies and individual needs. Conventional nasal dilator devices on the market mainly include disposable patch-type devices and integrated nasal expansion devices, with the integrated nasal patch structure being the most common. While these devices can improve nasal ventilation to some extent, they generally rely on a single mechanical stretching method, resulting in limited expansion effects and insufficient adaptability to diverse patient needs under different usage scenarios. Moreover, integrated fitting assemblies tend to experience reduced adhesiveness, detachment, or cause skin discomfort during long-term use, resulting in insufficient wearing comfort and durability. The market has introduced detachable or structurally simplified nasal dilator devices, such as magnetic-based products, which use modular or split designs to improve convenience and reusability. However, such devices still present deficiencies in safety, material biocompatibility, cost control, and manufacturing complexity. For example, magnetic components may pose risks in terms of attraction strength and stability, some materials may cause skin or mucosal discomfort, and multi-component designs increase manufacturing costs and operational complexity. In contrast, the adjustable nasal dilator device of this disclosure allows the expansion force and angles to be freely adjusted according to individual nasal anatomy. This design enhances wearing comfort and structural stability while ensuring durability and safety. The modular and adjustable structure enables adaptation to a broader patient population and meets long-term usage requirements, providing advantages over conventional devices in terms of safety, comfort, durability, and cost-effectiveness, and demonstrating significant innovation and practical value.
2. Specifically, with respect to adaptability and flexibility, the adjustable nasal dilator device of this disclosure includes adjusting components that allow precise modulation according to the patient's nasal anatomy, nasal wing width, and individual usage habits. The device enables patients to adjust both the magnitude and angles of the expansion force in different usage scenarios, achieving a highly accurate fit and significantly improving nasal ventilation efficiency and breathing smoothness. Patients may encounter various conditions in daily life, including changes in sleep posture, differences in environmental humidity and temperature, variations in respiratory states at different times, and minor physiological changes in the nasal cavity, all of which affect nasal ventilation requirements. The adjustable nasal dilator device addresses these diverse needs, allowing patients to obtain a personalized and comfortable experience with stable expansion effects without the need to frequently replace devices of different sizes or specifications. Furthermore, the adjustable functionality reduces interruptions due to discomfort or improper fit, enhances long-term compliance, and improves overall quality of life, thereby providing comprehensive support for respiratory health while balancing flexibility, comfort, and effectiveness.
3. With respect to performance, the adjustable nasal dilator device of this disclosure provides multiple additional advantages. First, in other adjustable devices available in the market, insufficient design of the adjusting mechanism often leads to rebound, deformation, or displacement during use, resulting in ineffective expansion or instability. To address this, the disclosure introduces an innovative integrated adjustment-and-locking mechanism, which allows angle adjustments to be performed flexibly while maintaining the preset position stably without requiring additional tools or auxiliary components. This mechanism resolves the conventional technical contradiction between "adjustable but unstable" and "stable but non-adjustable." Moreover, it ensures continuous output of expansion force and stability of the target effect, maintaining reliable fit and effective dilation even during sleep, changes in body posture, or daytime activities. The design also facilitates operation, enabling patients to quickly complete angle adjustment and position locking, enhancing usability and adaptability to diverse nasal anatomies and individual needs. Second, in one embodiment of the present disclosure, the adjusting assembly includes a knob structure and a tensioning member, with the adjusting mechanism in the form of a knob. In this configuration, patients can easily drive the tensioning member by rotating or pushing the knob, applying balanced tension to the two ends of the supporting member to achieve precise expansion of the nasal wings. This adjustment approach is simple and convenient, allowing patients to perform rapid adjustments and greatly improving operational portability. It lowers the usage threshold, reduces the risk of misuse, and is particularly suitable for elderly patients, children, or individuals with limited hand dexterity. In addition, the adjusting assembly of this disclosure provides superior expansion performance compared to adjusting mechanisms available in the market. Compared to conventional market devices that rely primarily on pre-set elastic materials for expansion, the adjusting assembly of this disclosure enables more precise modulation of the two ends of the supporting member with less applied force. During use, the force remains balanced and stable, significantly improving the expansion range and consistency. Third, in this adjusting mechanism, the adjusting assembly and the tensioning member work cooperatively, allowing simple operations to simultaneously adjust both ends of the supporting member, ensuring uniform tension distribution across both sides of the nose, reducing local pressure or discomfort, and improving patient wearing comfort.

4. Additionally, the nasal dilator device of the present disclosure provides the advantage of a reusable design. Many nasal dilator devices available in the current market are primarily designed for single-use or lack the capability for repeated adjustment. While such devices are simpler to manufacture, their limited usage cycle prevents repeated adjustment, and long-term use may negatively affect wearing comfort and overall user experience, making it difficult to meet patient demands for durability and personalized adaptation. In contrast, the disclosure described herein allows patients to avoid frequently replacing single-use products, significantly reducing usage and treatment costs. Moreover, the reusable nature of the device effectively minimizes waste generation, alleviates environmental impact, and aligns with principles of green and sustainable development.
5. In the present disclosure, the supporting member made of elastic material is configured to conform to the patient's skin during use. This material not only maintains the set shape after adjustment, preventing loss of expansion force due to rebound, but also ensures lightweight, low skin irritation, and long-term contact safety, allowing the patient to maintain comfort during extended use. In conventional nasal dilator devices, material selection often presents significant limitations: purely rigid materials can provide the necessary support but lack flexibility, potentially causing localized pressure and reducing wearing comfort; fully flexible materials, while soft and comfortable, are unable to provide sufficient expansion force and may lack stability over long-term use, leading to deformation or failure. To address these issues, this disclosure overcomes the limitations of purely rigid or flexible materials, optimizing the material properties to achieve a balance between functionality, stability, and comfort. In one embodiment, a composite material strategy is employed, allowing the nasal dilator device to be more suitable for use and to work in coordination with the adjusting assembly, thereby providing significant innovation and practical value.

BRIEF DESCRIPTION OF THE DRAWINGS

FIG. 15 is a schematic view showing the first direction and the second direction opposite in the adjusting mechanism according to multiple embodiments of the present disclosure;

FIGS. 16A and 16B are schematic views illustrating different configurations of a tensioning member arranged in a crossed or parallel manner according to multiple embodiments of the present disclosure;

FIGS. 17A and 17B are schematic views showing a middle section of the supporting member configured with a serrated structure according to multiple embodiments of the present disclosure;

FIG. 18 is a schematic view of another knob-type adjusting mechanism in an embodiment of the present disclosure;

FIGS. 27A, 27B and 27C are schematic views of the nasal dilator device with a comfort layer in an embodiment of the present disclosure;

DETAILED DESCRIPTION

Figure 1:
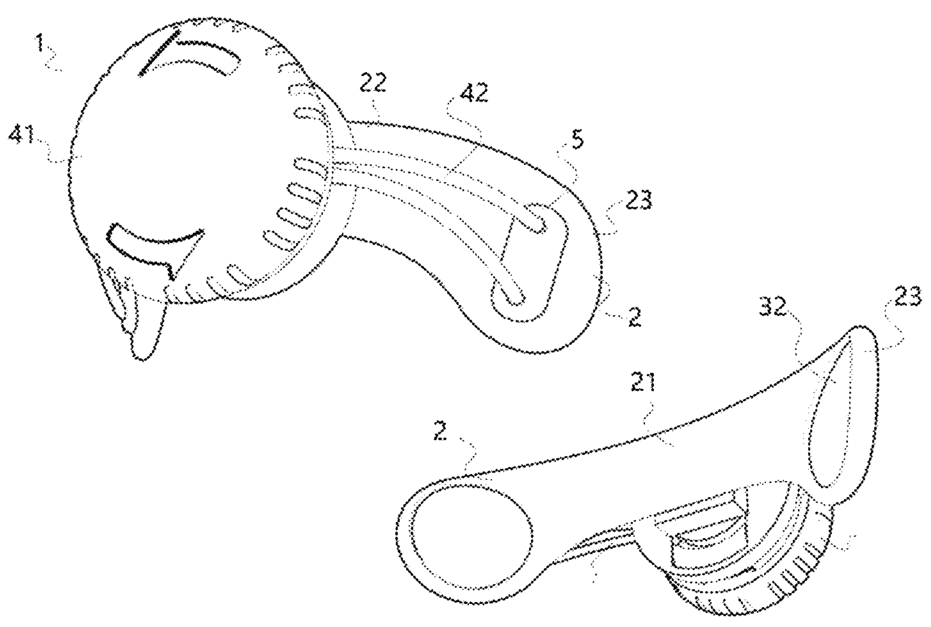
FIG. 1 is a perspective view of a nasal dilator device according to multiple embodiments of the present disclosure.
Figure 2:
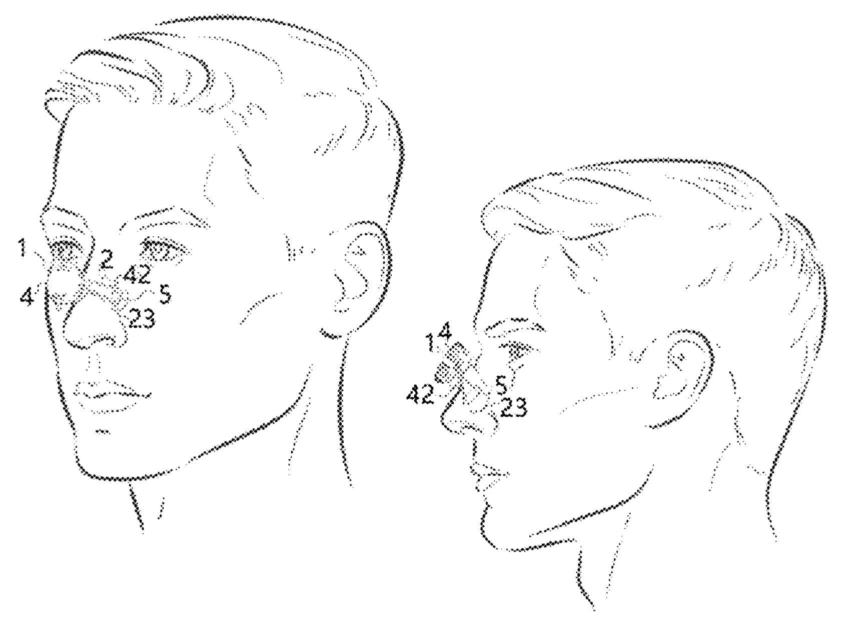
FIG. 2 is a schematic view of the nasal dilator device worn on a patient according to multiple embodiments of the present disclosure.
Figure 3:
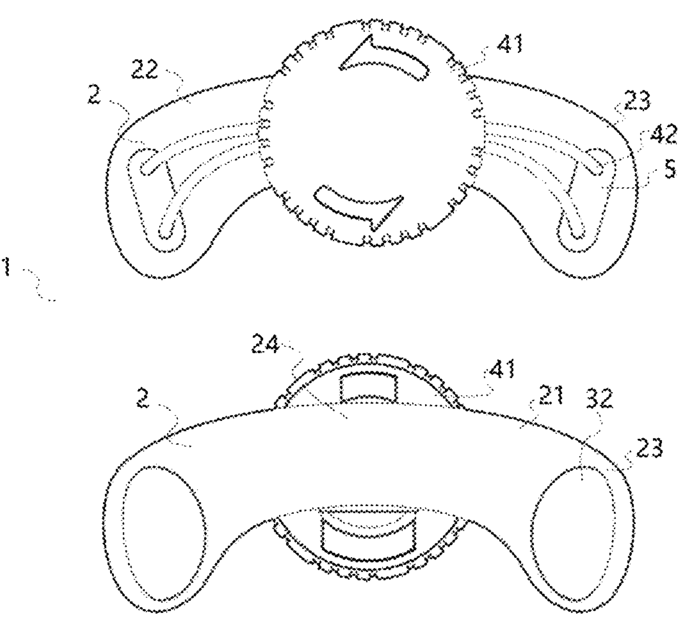
FIG. 3 is a front view and rear view of the nasal dilator device in orthogonal projection according to multiple embodiments of the present disclosure.
Figure 4:
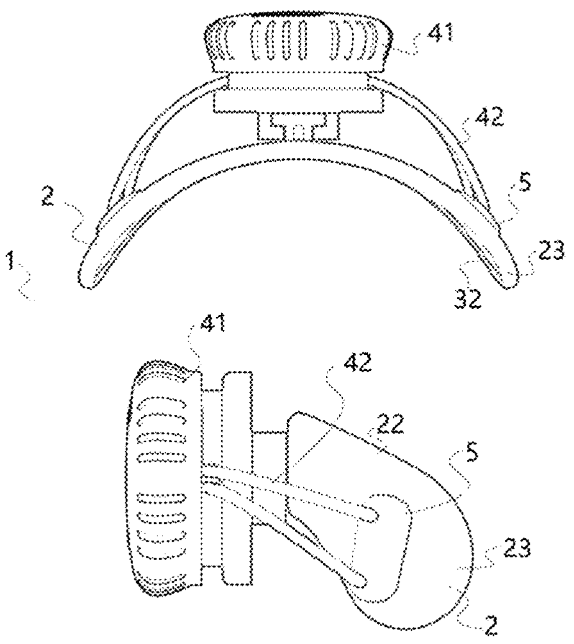
FIG. 4 is a top view and side view of the nasal dilator device in orthogonal projection according to multiple embodiments of the present disclosure.
Figure 5:
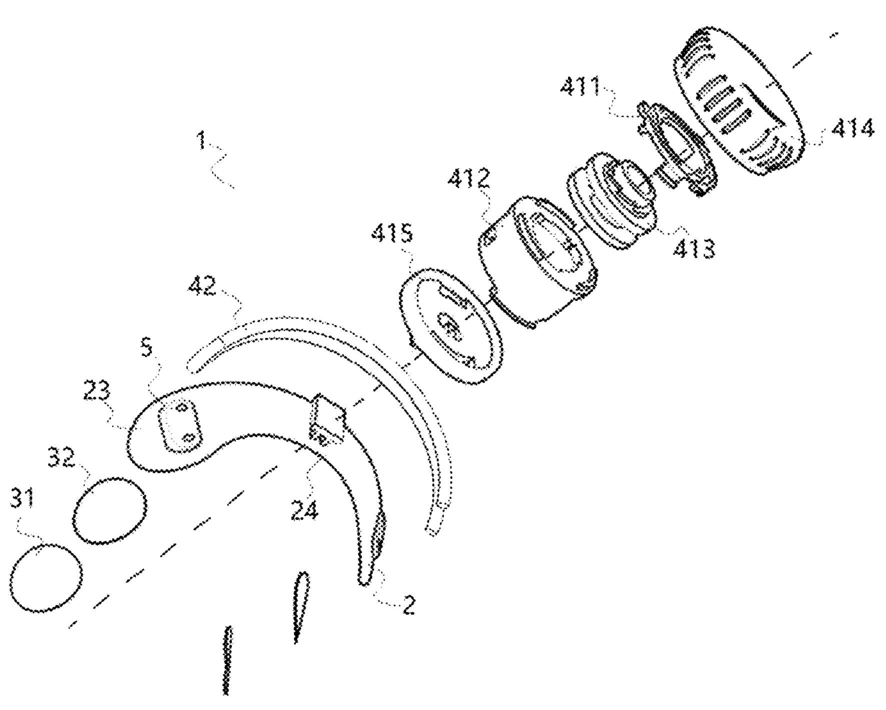
FIG. 5 is an exploded view of a structure of the nasal dilator device according to multiple embodiments of the present disclosure.
Figure 6:
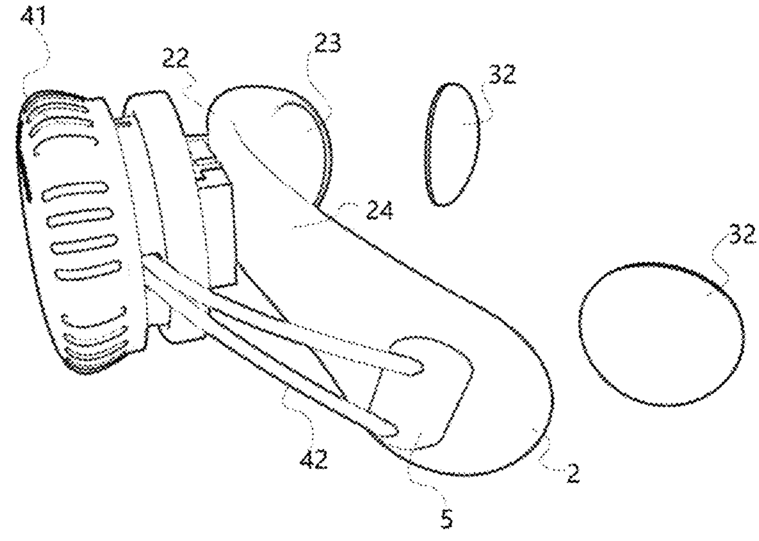
FIG. 6 is a schematic view illustrating a connection between a second connecting portion of a fitting assembly and a supporting member according to multiple embodiments of the present disclosure.
Figure 7:
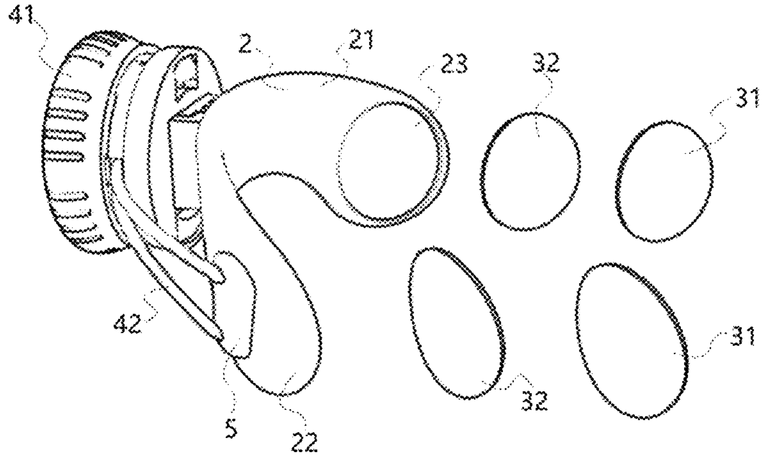
FIG. 7 is a schematic view showing the engagement of the fitting assembly according to multiple embodiments of the present disclosure.

To make the objectives, features, and advantages of the present disclosure more apparent and easier to understand, several specific embodiments are described in detail below with reference to the accompanying drawings. Numerous specific details are set forth in the following description to facilitate a thorough understanding of the present disclosure. However, the present disclosure may be implemented in many different ways other than those specifically described herein. Modifications and equivalents made by those skilled in the art without departing from the spirit and scope of the present disclosure are also intended to be covered. Therefore, the scope of the present disclosure is not limited to the specific embodiments described below.

Compared with the nasal dilator devices of the prior art, the nasal dilator device disclosed herein achieves substantial improvements and enhancements in multiple aspects. First, an innovative adjusting assembly is introduced, allowing the device to adapt precisely to the nasal conditions of the patient under different physiological states, thereby achieving a personalized expansion effect and significantly improving the flexibility and adaptability of the device during actual use. Second, the design of the adjusting mechanism is further refined so that, after adjustment, the mechanism can automatically or semi-automatically maintain its set state, which simplifies the operation process of the nasal dilator device and makes it more user-friendly for different patient groups. In addition, the materials of the device are carefully optimized to ensure that sufficient expansion force is maintained while gently conforming to the nasal wings, thereby avoiding localized pressure, friction, or allergic reactions, and improving wearing comfort and compliance.

As shown in FIGS. 1 to 26 and FIGS. 27A to 27C, various views of the nasal dilator device are illustrated, including perspective views, orthogonal projection views, structural views, and wearing demonstrations.

Several structural examples of the nasal dilator device of the present disclosure are described below in conjunction with specific embodiments.

Embodiment 1

The nasal dilator device 1 of the present embodiment includes a supporting member 2 having a first side 21 facing the patient's face during use and a second side 22 opposite to the patient's face. The supporting member 2 further has at least two end portions 23 arranged opposite to each other and configured to laterally fit the sides of the patient's nose during use. The supporting member 2 is at least partially made of an elastic material and has a tendency for both ends to extend downward. The device further includes a fitting assembly 3 having at least two first connecting portions 31 attached to the patient's nose in a use state and at least two second connecting portions 32 at least partially connected to the left and right ends of the supporting member 2. The fitting assembly 3 is configured to mutually engage during use. The device also includes an adjusting assembly 4 having at least one adjusting mechanism 41 and at least one tensioning member 42. The adjusting assembly 4 is configured to engage with the supporting member 2 and, during use, the adjusting mechanism 41 controls the tensioning member 42 to adjust the angles of the left and right ends of the supporting member 2. The adjusting assembly 4 engages with the supporting member 2 via a fixing structure 5, with the fixing structure 5 disposed at least at the left and right ends of the supporting member 2. The adjusting mechanism 41 is configured for incremental adjustment and can be fixed after adjustment. The adjusting mechanism 41 has at least a first mechanism configured to tension the tensioning member 42 and a second mechanism configured to relax the tensioning member 42. The operation of the adjusting assembly 4 is such that an acting force is applied to the adjusting mechanism 41, the acting force drives the tensioning member 42 and transmits to the left and right ends 23 of the supporting member 2, causing at least portions of the left and right ends to lift toward the second side 22. The length of the tensioning member 42 is greater than its width.

Figure 11:
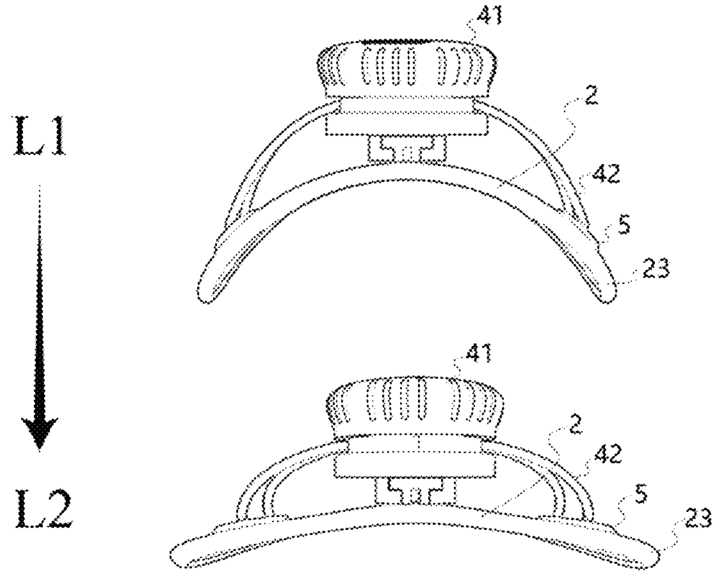
FIG. 11 is a schematic view showing an expansion effect achieved by the nasal dilator device according to multiple embodiments of the present disclosure.
Figure 12:
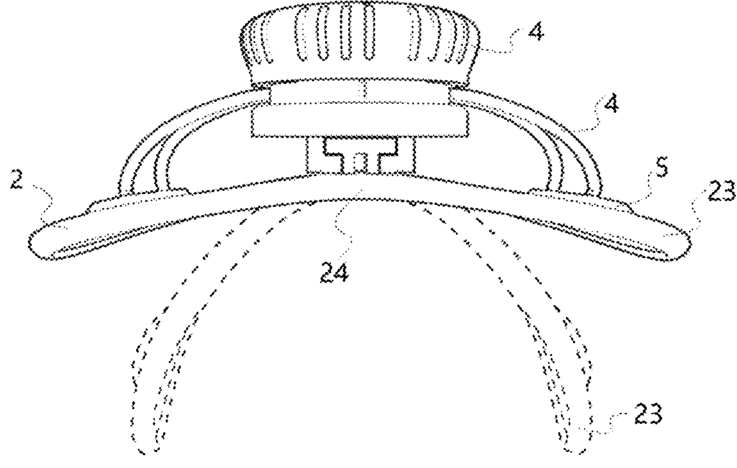
FIG. 12 is a schematic view illustrating a change in expansion angle of the nasal dilator device according to multiple embodiments of the present disclosure.
Figure 24:
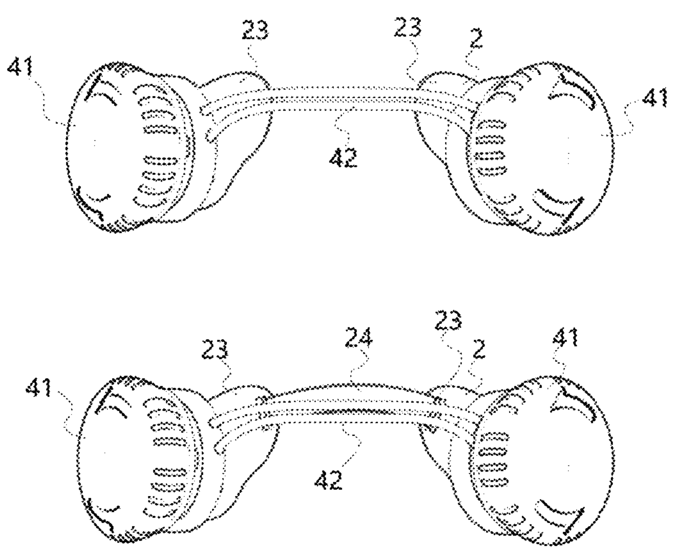
FIG. 24 is a schematic view showing different forms of the supporting member in an embodiment of the present disclosure.

Specifically, the nasal dilator device 1 includes a supporting member 2, which is generally in the form of a thin sheet with an overall length greater than or equal to its height and is at least partially bent in one direction, the bending direction facing the patient's face and conforming to it during use. The supporting member 2 has a first side 21 facing the patient's face during use and a second side 22 opposite to the patient's face. The first side 21 is configured to at least partially contact the patient's face during use, and the second side 22 is configured to at least partially engage with the adjusting assembly 4. The supporting member 2 also has at least two end portions 23 arranged opposite to each other and configured to laterally fit the sides of the patient's nose during use. The end portions 23 are important structural elements of the nasal dilator device 1. The supporting member 2 can consist only of the two end portions 23 (as shown in FIG. 24), or further include a middle section 24 connecting the two end portions 23. The end portions 23 and the middle section 24 can be made of the same material or different materials. Preferably, the middle section 24 and the two end portions 23 are integrally formed with a continuous curvature, such that the supporting member 2 is an integrated thin sheet including the middle section 24 and the left and right end portions 23. In other cases, the middle section 24 and the two end portions 23 are separate components connected by bonding, mechanical connection, magnetic connection, or other suitable methods, allowing for modularization. The middle section 24 can take various forms, including but not limited to a thin sheet or a rope sleeve. The end portions 23 can also have various shapes, such as circular, oval, or polygonal, to accommodate different nasal anatomies and personalized needs of patients. The fitting assemblies 3 of the two end portions 23 are generally symmetrical or equivalent in shape, but in some cases, the two end portions 23 may be designed asymmetrically to achieve better fitting or different functional effects. Overall, the supporting member 2 has a tendency for the left and right ends to extend downward, forming a contour that is higher in the middle and lower at the sides. The gradually downward-extending shape allows the supporting member 2 to conform to the natural curve of the patient's nose and achieve closer contact with the nasal skin, reducing local pressure and discomfort. In addition, the supporting member 2 has, at least at one position, a curvature in the vertical direction facing the patient's face, which allows it to more naturally conform to the physiological curve of the patient's face during use, improving comfort and stability while reducing local pressure and the risk of slippage. When the adjusting assembly 4 is operated to adjust the angles of the left and right ends of the supporting member 2 (as shown in FIGS. 11 and 12, the supporting member 2 can be adjusted from a length L1 to a length L2), the presence of this curvature effectively distributes deformation stress on the structure, preventing excessive twisting or irregular deformation of the supporting member 2, thereby maintaining the overall structural balance and reliability, ensuring consistent fitting performance and long-term durability of the device.

Figure 8:
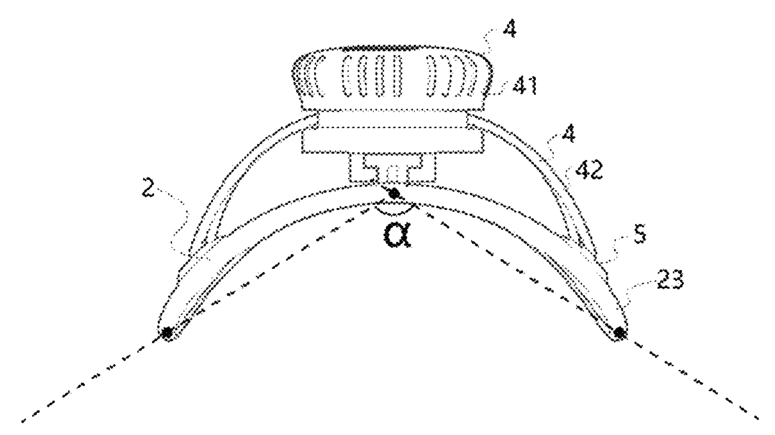
FIG. 8 is a schematic view showing an angle of the supporting member in the nasal dilator device under normal, unloaded conditions according to multiple embodiments of the present disclosure.
Figure 9:
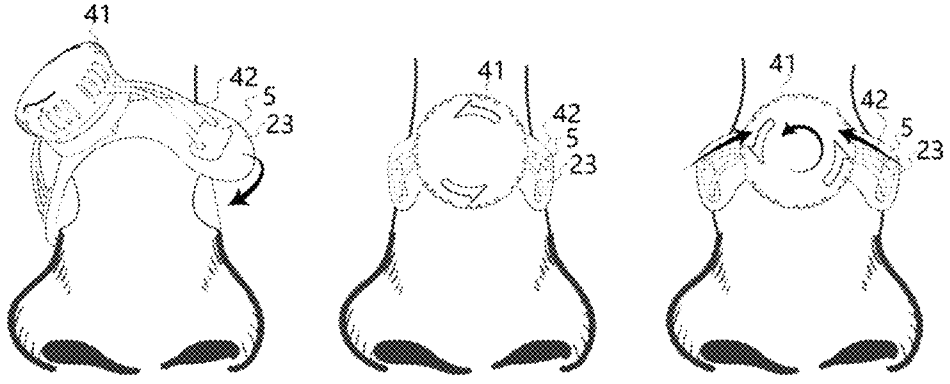
FIG. 9 is a schematic view showing the nasal dilator device in use when worn according to multiple embodiments of the present disclosure.

To ensure comfort during patient use, the supporting member 2 is designed to have a thickness ranges from 0.1 mm to 20 mm, while maintaining sufficient flexibility and lightweight characteristics, and providing adequate structural strength and stability when a relatively large expansion force is required. The specific thickness of the supporting member 2 can be flexibly adjusted according to different materials and their mechanical properties. The length of the supporting member 2 ranges from 9 mm to 150 mm, fully considering the variability of nasal anatomy among different populations and the required coverage of the nasal cavity during use. In a normal state without applied force, the angle range of the left and right sides of the supporting member 2 is 30° to 180° (as shown in FIG. 8, where a ranges from 30° to 180°).

Figure 26:
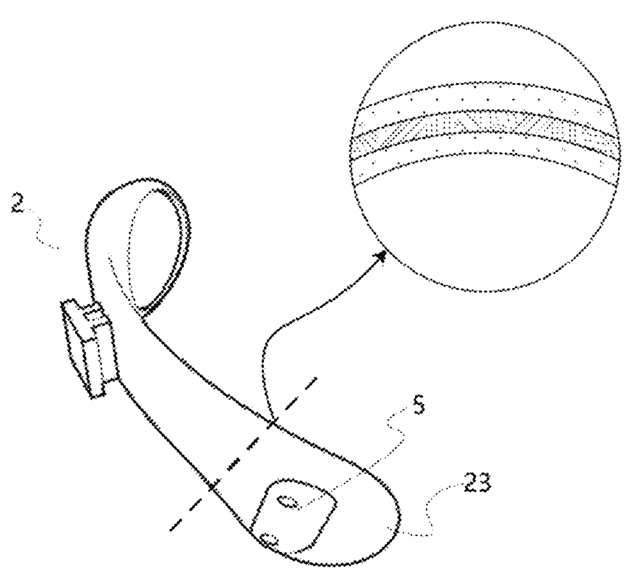
FIG. 26 is a schematic view showing the supporting member of the nasal dilator device as a multi-layer composite structure in an embodiment of the present disclosure.

In this embodiment, the supporting member 2 is at least partially made of an elastic material, which can be understood as a material that deforms under applied force and substantially returns to its original shape when the force is removed. The material includes one or more of the following: thermoplastic elastomer (TPE), thermoplastic polyurethane elastomer (TPU), silicone rubber, copolyether ester elastomer (COPE), ethylene-vinyl acetate copolymer (EVA), malleable metal sheets, or multilayer composite structures (as shown in FIG. 26). The Shore hardness of the material is generally controlled between 30 A and 80 A to achieve a balance between structural stability and wearing comfort.

Figure 25:
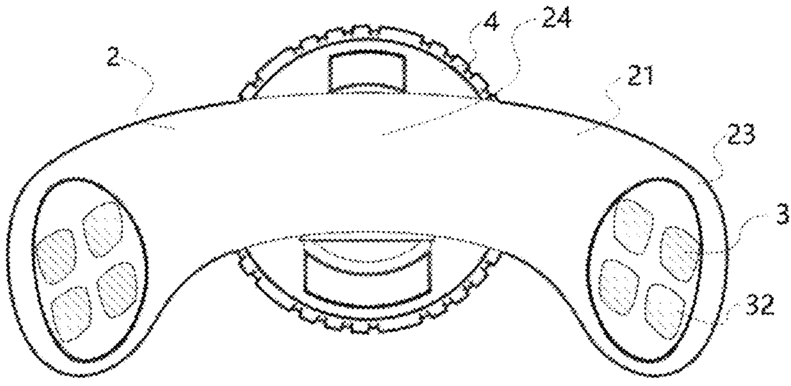
FIG. 25 is a schematic view illustrating the fitting component with more than two first connecting portions and second connecting portions in an embodiment of the present disclosure.

The fitting assembly 3 has at least two first connecting portions 31 attached to the patient's nose in a use state, and at least two second connecting portions 32 at least partially connected to the left and right ends of the supporting member 2. The fitting assembly 3 is configured to mutually engage during use. The fitting assembly 3 can be designed in various shapes according to different usage requirements, including but not limited to circular, oval, or polygonal shapes. Generally, the fitting assembly 3 has two first connecting portions 31 and two second connecting portions 32. In some other situations, to make the nasal cavity expansion more secure, there can simultaneously be three or more first connecting portions 31 and second connecting portions 32 (as shown in FIG. 25). The second connecting portions 32 and the supporting member 2 can be detachably connected (including mechanical connection, magnetic connection, or hook-and-loop connection) or non-detachably connected (including integral molding processes, adhesive bonding, ultrasonic welding, hot pressing technology, and stitching connection). Specifically, the fitting assembly 3 and the supporting member 2 are joined by at least one method, such as buckle connection, adhesive connection, magnetic connection, threaded connection, or hook-and-loop fastener. If the fitting assembly 3 is connected to the supporting member 2 via chemical adhesive or hot melt form, the fitting assembly 3 may use materials with good adhesive affinity such as polyurethane (PU) or EVA, and have a microporous texture or guiding groove on the surface to enhance the bonding strength and durability. The fitting assembly 3 can also be composed of nylon, polyester, nylon-polyester blends, TPU-coated nylon, brushed fabric materials, or polypropylene hot-pressed hooks. In some special cases, the fitting assembly 3 only has the first connecting portion 31 configured to directly connect with the supporting member 2. When the second connecting portion 32 and the supporting member 2 are detachably connected, during use, the second connecting portion 32 needs to be adhered to the corresponding positions on the left and right ends of the supporting member 2, and the first connecting portion 31 needs to be adhered to the corresponding positions on the sides of the patient's nose. Subsequently, the first connecting portion 31 and the second connecting portion 32 are correspondingly adhered and connected for use. The two mutually connected fitting assemblies 3 have corresponding shapes. The connection between the fitting assemblies 3 (or the fitting assembly 3 and the end portion 23) can utilize various methods, including but not limited to adhesive connection, mechanical mechanism connection (e.g., buckle or slot-in type), magnetic connection, or hook-and-loop fastener connection. In actual use, the connection force generated between the fitting assemblies 3 (or the fitting assembly 3 and the end portion 23) is in the range of 2 gf to 200 gf.

The dimension design of the fitting assembly 3 is generally controlled within the range of 0.05 $cm^2$ to 20 $cm^2$, to balance sufficient connection area with wearing comfort. Generally, the sum of the areas of the first connecting portion 31 or the second connecting portion 32 of the fitting assembly 3 is less than or equal to the sum of the areas of the first side 21 of the supporting member 2. In some special cases, the sum of the areas of the first connecting portion 31 or the second connecting portion 32 of the fitting assembly 3 may also be greater than the sum of the areas of the first side 21 of the supporting member 2.

The materials for the first connecting portion 31 and the second connecting portion 32 can be the same or different. Specifically, the materials can be selected from elastomers or flexible film materials that possess high compliance and skin compatibility, including but not limited to medical-grade silicone, thermoplastic elastomer (TPE), polyurethane film, and textile composite materials, along with other environmentally friendly and reusable materials. Furthermore, composite materials may be used to achieve better usage effects. Preferably, this part is made of medical-grade skin-adhering material, possessing good breathability, skin-friendliness, and hypoallergenicity to ensure skin comfort and safety during long-term wear. This part may be a soft adhesive layer or a replaceable medical patch, facilitating easy replacement and maintenance. In some implementations, these materials are a multilayer composite structure. The inner layer utilizes medical-grade silicone or TPE as the skin-friendly coating that directly contacts the skin. The middle layer may employ a textile composite material or a film layer to enhance strength. The textile composite material incorporates environmentally friendly fibers such as organic cotton, bamboo fiber, or recycled polyester fiber. The film layer is an ultra-thin and flexible polymer material film, typically made of polyurethane or polyvinyl fluoride, which is waterproof and sweatproof, as well as environmentally friendly, biodegradable, and highly breathable, and is used to cover the surface layer of the adhering material. The outer layer serves as a protective layer or fixing layer and is combined with the end portion 23 via adhesive bonding or mechanical connection to achieve secure fitting and facilitate easy cleaning and repeated use.

Figure 10:
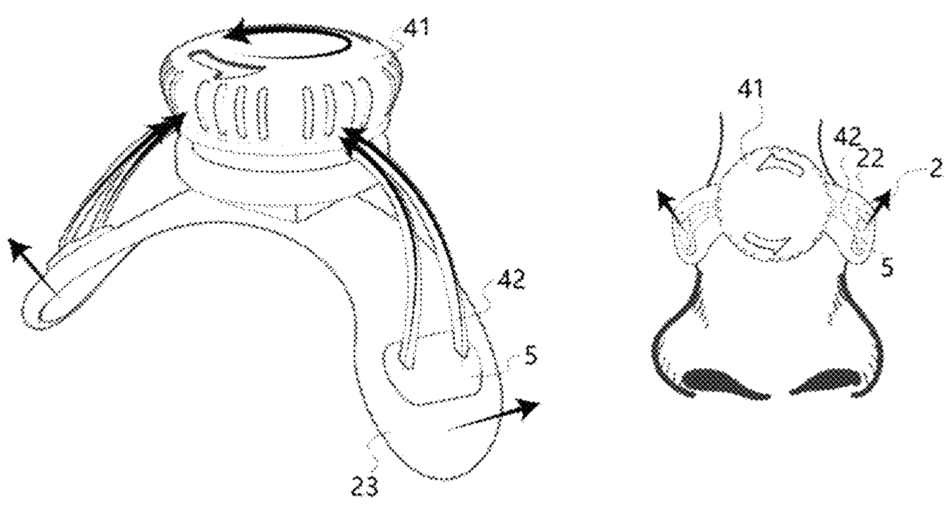
FIG. 10 is a schematic view illustrating forces of the nasal dilator device during adjustment according to multiple embodiments of the present disclosure.
Figure 14:
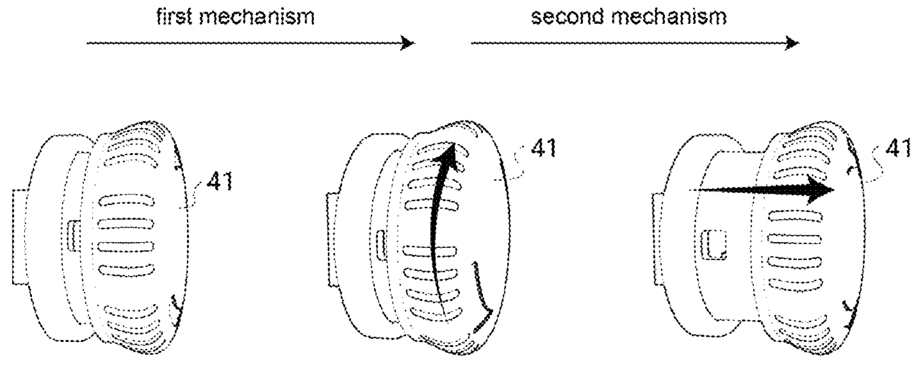
FIG. 14 is a schematic view showing a first direction and a second direction perpendicular in an adjusting mechanism according to multiple embodiments of the present disclosure.

The adjusting assembly 4 includes at least one adjusting mechanism 41 and at least one tensioning member 42, the adjusting assembly 4 being configured to engage with the supporting member 2 and, during use, the adjusting mechanism 41 controls the tensioning member 42 to adjust the angles of the left and right ends of the supporting member 2 (as shown in FIG. 10). The operation of the adjusting assembly 4 is such that an acting force is applied to the adjusting mechanism 41, the acting force drives the tensioning member 42 and transmits to the left and right ends 23 of the supporting member 2, thereby causing at least part of the structures at the left and right ends to lift toward the second side 22. Specifically, the adjusting mechanism 41 has at least a first mechanism configured to tension the tensioning member 42 and a second mechanism configured to relax the tensioning member 42. During the adjustment of the first mechanism, the adjusting mechanism 41 generates an acting force in a first direction, and during the adjustment of the second mechanism, the adjusting mechanism 41 generates an acting force in a second direction. The first mechanism is configured to apply force in the first direction to tension the tensioning member 42, and the second mechanism is configured to apply force in the second direction to relax the tensioning member 42. In this embodiment, the first direction and the second direction are perpendicular to each other (as shown in FIG. 14), and in this case, when a force is applied in the second direction, the supporting member 2 immediately returns to its original state. In some other implementations, the first direction and the second direction are completely opposite or at least partially opposite (as shown in FIG. 15). In one form, the adjusting mechanism 41 is designed for incremental adjustment. More specifically, the adjustment of the first mechanism can be set as an incremental adjustment, meaning that each operation produces a quantified adjustment effect, allowing the tensioning force of the tensioning member 42 to change in a stepwise and controllable manner, thereby achieving a more precise adjustment effect. Incremental adjustment can effectively avoid discomfort caused by excessive tensioning or insufficient expansion force caused by inadequate relaxation, allowing the patient to self-adjust between comfort and stability and thereby achieve an optimal balance. In some cases, the adjusting assembly 4 is configured to produce sound during adjustment to provide audible feedback, enabling the patient to perceive and confirm the extent of adjustment. In some cases, the adjusting assembly 4 is configured to produce tactile feedback during adjustment. To ensure symmetrical adjustment of the left and right sides, the adjusting assembly 4 is generally disposed at the middle portion of the nasal dilator device 1, or multiple adjusting assemblies 4 are arranged oppositely at the left and right sides of the nasal dilator device 1. In some special cases, the adjusting assembly 4 may also be positioned asymmetrically on the nasal dilator device 1.

Figure 13:
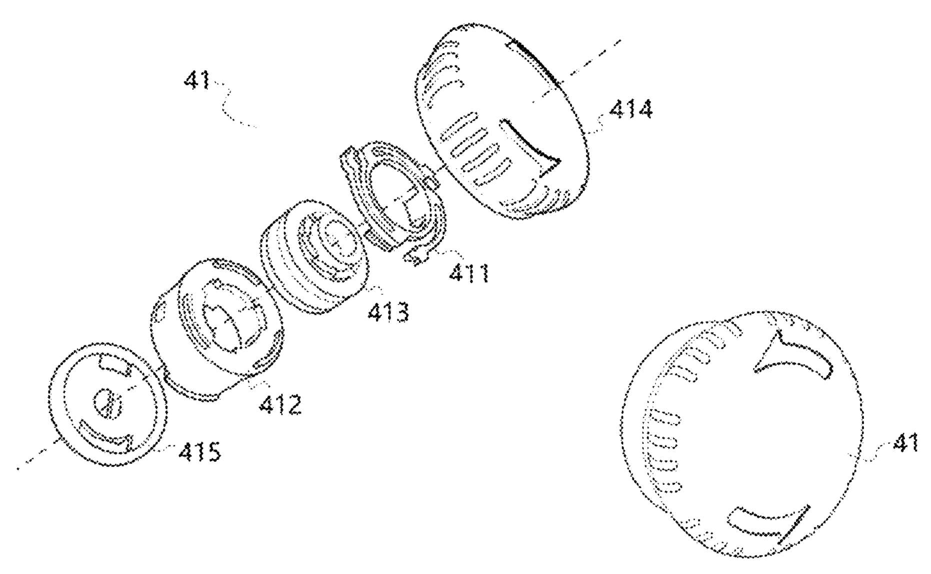
FIG. 13 is an exploded schematic view of a knob-type adjusting mechanism in an embodiment of the present disclosure.
Figure 28:
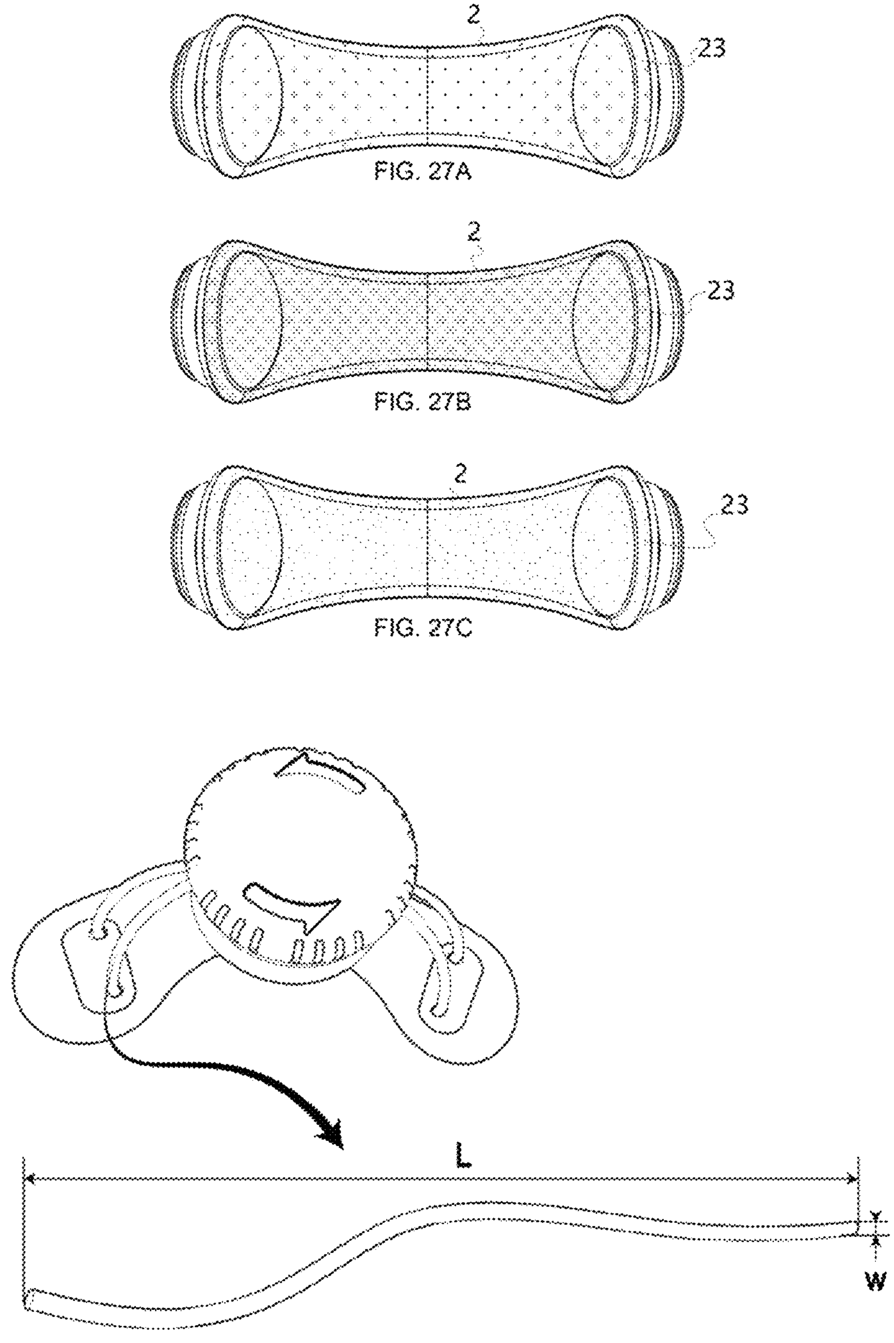
FIG. 28 is a view illustrating a length and width of the tensioning member according to multiple embodiments of the present disclosure.

The adjusting assembly 4 can have various forms, meaning that the adjusting mechanism 41 and the tensioning member 42 may take different structures. The adjusting mechanism 41 can be of any form that adjusts the tensioning member, and the tensioning member 42 can be of any form that applies a pulling force to the supporting member 2. In one case, the adjusting mechanism 41 is a knob structure (as shown in FIGS. 13 and 18), and the tensioning member 42 is a drawstring-type structure. In this form, the adjusting mechanism 41 controls the tension of the tensioning member 42 through rotational operation, thereby adjusting and maintaining the expansion angle of the supporting member 2. More specifically, the adjusting mechanism 41 includes at least a ratchet wheel 411, a housing 412, a fastener 413, a dial 414, and a base member 415. The ratchet wheel 411 is coupled with the housing 412, the fastener 413 is arranged inside the housing 412 and configured to connect with the dial 414, and the housing 412 is also connected with the base member 415 (as shown in FIG. 13). The dial 414 has an internal gear structure, and the ratchet wheel 411 cooperates with the gear structure to form a one-way rotation mechanism, which provides incremental adjustment and tactile and/or audible feedback. In one form, the fastener 413 and the dial 414 are integrated, and the dial 414 and the housing 412 are merely placed in relation. The outer surface of the dial 414 can be provided with rotation marks or anti-slip textures. The tensioning member 42 can be a high-strength linear element resistant to tearing, such as aramid fiber, polyester fiber, high-tenacity polyethylene fiber, or coated steel cable. The tensioning member 42 has a length greater than its width (as shown in FIG. 28, where the length L and the width W represent the length and width of a single linear element). In this embodiment, the tensioning member 42 passes through the fastener 413 and the housing 412 to jointly form a tightening structure. The tensioning member 42 may be arranged in parallel inside the adjusting mechanism 41 or arranged in a crossed manner inside the adjusting mechanism 41 (as shown in FIGS. 16A and 16B). The tensioning member 42 is also fixed to the two end portions 23 of the supporting member 2. During tightening adjustment, rotation of the dial 414 drives the ratchet wheel 411 to rotate in one direction through the internal gear structure of the dial 414. At the same time, the rotation of the dial 414 drives the fastener 413 to rotate, while the housing 412 remains stationary. As a result, the tensioning member 42 gradually winds around the outer circumference of the fastener 413 and tightens. As the tensioning member 42 is gradually tightened, the pulling force acts on the two end portions 23 connected thereto, causing the two end portions 23 to gradually deform in the direction of the pulling force, thereby increasing the angle formed by the left and right ends of the supporting member 2. Ultimately, an outward expansion force is applied to both sides of the patient's nasal wings, physically expanding the nasal cavity. The adjusting assembly 4 is further configured to automatically lock the current state after each adjustment of the first mechanism, preventing rebound of the supporting member 2. In the knob-type adjusting assembly 4, the locking mechanism is based on the ratchet wheel 411 and the meshing gear structure. The gear structure may be integrated inside the dial 414, may be set as a separate component, or may be integrated with other components. The incremental adjusting mechanism is also achieved through this structure. The adjusting mechanism 41 is further configured to form a release state when an acting force is applied in the second direction. In one form, under this force, the ratchet wheel 411 disengages from the meshing gear structure, and at the same time, the fastener 413 is released (not connected with the dial 414 for synchronous rotation), so that the tension of the tensioning member 42 is released and the supporting member 2 returns to its initial state. In the limit state, the adjusting assembly 4 drives the supporting member 2 to deform within an angle range of 0° to 150°, resulting in a nasal expansion amplitude between 0.1 mm and 20 mm. The diameter of each knob structure is preferably 10 to 25 mm, and the thickness is 3 to 10 mm.

Figure 20:
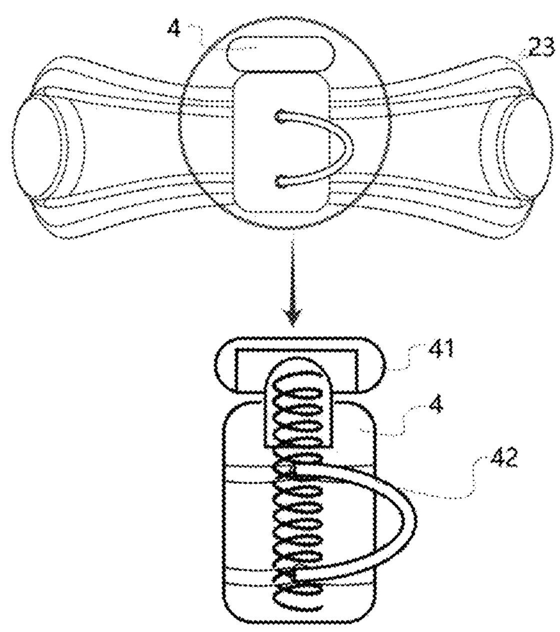
FIG. 20 is a schematic view of the nasal dilator device according to an embodiment of the present disclosure, in which the adjusting assembly is implemented as a drawstring-type structure.

In other cases, the adjusting assembly 4 can take other forms, including a cord structure, a ratchet engagement structure, or a malleable metal sheet. In one form, the adjusting mechanism 41 includes a housing 412, an embedded spring assembly, and a sliding block internally provided with a locking tooth structure, while the tensioning member 42 is a cord structure that passes through the sliding block and is distributed along a sliding channel (as shown in FIG. 20). During use, the patient can push the sliding block inward, causing it to drive the cord structure along the sliding channel to tighten, which causes the two ends of the supporting member 2 to expand outward and form an expansion angle. After reaching the desired angle, releasing the sliding block allows the spring to automatically return it to the original position and engage the locking teeth, thereby locking the current angle. If a release adjustment is needed, the sliding block can be gently pulled outward to disengage from the locking teeth and release the tension, allowing the expansion amplitude to be reset. The pulley assembly is configured to guide the movement of the cord structure and enhance traction efficiency, including one or more small pulleys arranged on the middle section 24 or near the fitting assembly 3. After the cord structure passes around the pulleys, greater pulling force can be achieved within a limited space. The pulley assembly allows the cord structure to change the opening angle of the two ends of the supporting member 2 during tightening, and the target position can be stably fixed through rack engagement or wedge limiting, preventing rebound of the angle after adjustment.

Figure 21:
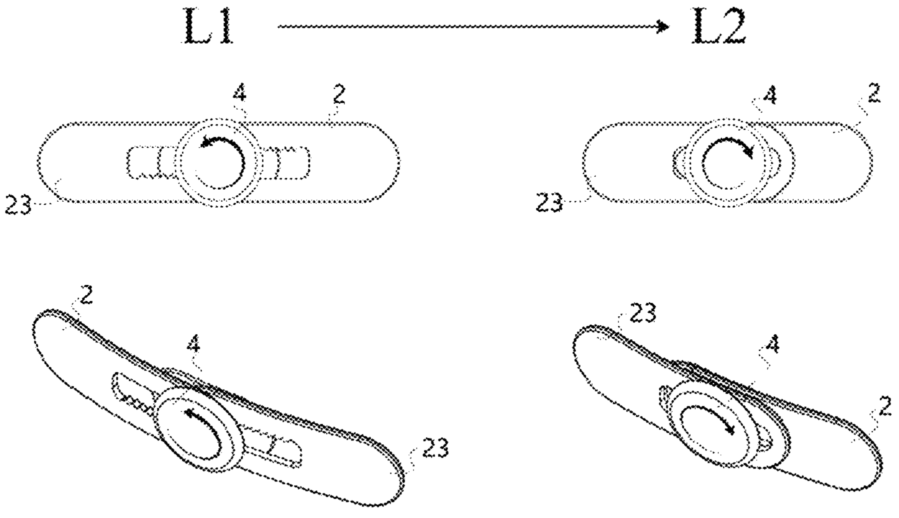
FIG. 21 is a schematic view of the ratchet engagement type adjusting assembly in an embodiment of the present disclosure.
Figure 22:
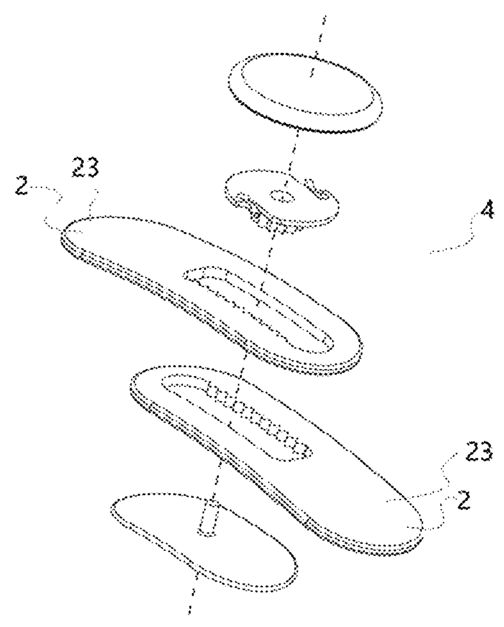
FIG. 22 is a disassembled view showing a structure of the adjusting assembly in FIG. 21.

In one form, the adjustment of the adjusting assembly 4 is performed through a ratchet engagement mechanism (as shown in FIGS. 21 and 22, the length of the supporting member 2 varies within the range of L1-L2 through adjustment by the adjusting assembly 4). In this case, the adjusting mechanism 41 is a central connecting member, and the tensioning member 42 is a serrated hinged structure. The supporting member 2 is divided into left and right portions to form a movable hinge, and the hinge portion is provided with a serrated limiting rack. During adjustment, the patient can push the connecting segment along the direction of the rack to the desired angle, and the engagement structure automatically locks in place to maintain the state. When it is necessary to change the angle, pressing a release button or sliding an unlocking member disengages the engagement lock, allowing the angle to be reset. This structure provides the advantages of simple physical adjustment, reliable construction, and long service life for repeated adjustments.

Figure 29:
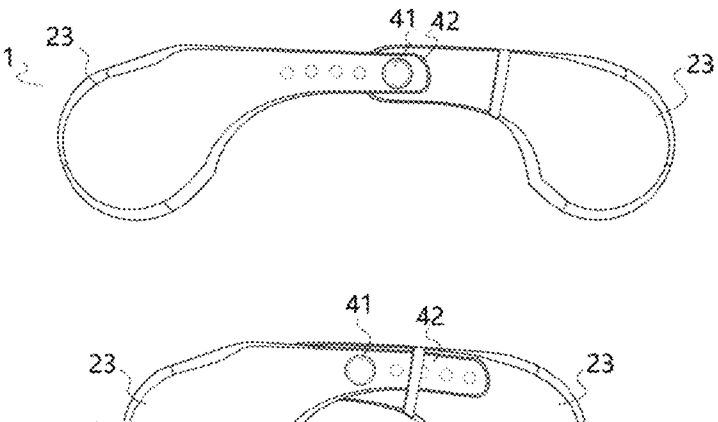
FIG. 29 is a schematic view of a pin-and-buckle type adjustment in an embodiment of the present disclosure.

In one form, the adjustment of the adjusting assembly 4 is performed through a pin-and-buckle mechanism (as shown in FIG. 29). In this case, the adjusting mechanism 41 is a pin-and-buckle structure, and the tensioning member 42 is a limiting hole structure. The supporting member 2 is divided into left and right portions, with one side provided with multiple rows of limiting holes and the other side configured with a pin-and-buckle. The pin can be inserted into the limiting holes and fixed in position by the locking element of the buckle structure. During adjustment, the patient can insert the pin into different limiting holes to achieve precise adjustment of length or angle. When it is necessary to change the position, the locking element can be lightly pressed to release the fixation, and the pin can be reinserted into the target hole.

Figure 30:
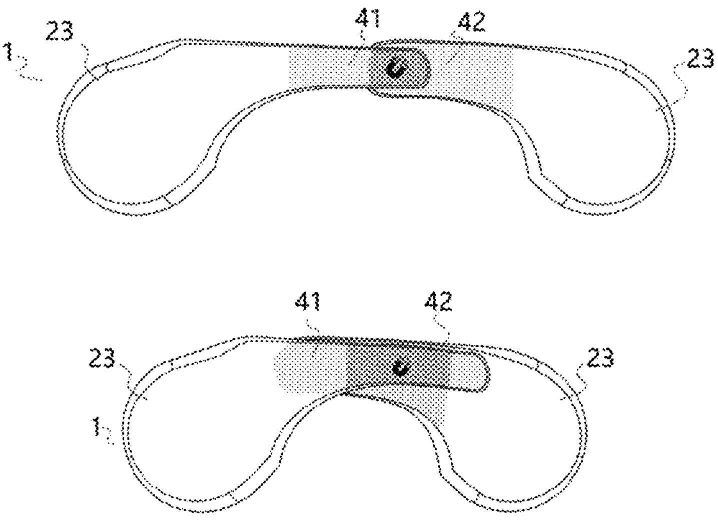
FIG. 30 is a schematic view of a magnetic positioning-type adjustment in an embodiment of the present disclosure.

In one form, the adjusting assembly 4 is configured as a magnetic positioning-type adjustment (as shown in FIG. 30). In this case, the adjusting mechanism 41 and the tensioning member 42 include multiple magnetic attraction nodes disposed on the supporting member 2. During use, the patient can attach the magnetic nodes of the tensioning member 42 to corresponding magnetic positions on the supporting member 2 to achieve different levels of tightness. By changing the selected attachment points, quick adjustments can be realized. This configuration provides the advantages of a simple adjustment process, no mechanical wear, and a long service life for repeated use.

In one form, the adjustment of the adjusting assembly 4 is performed through a threaded screwing mechanism. The adjusting mechanism 41 includes a supporting member 2 end portion 23 with external threads and a knob component with internal threads, while the tensioning member 42 is a cord structure connected to the knob component. During adjustment, the patient can achieve gradual lengthening or shortening of the tensioning member 42 by screwing in or out the knob, thereby accomplishing the desired adjustment. This structure provides advantages of high adjustment precision, strong locking stability, and durable construction.

Figure 19:
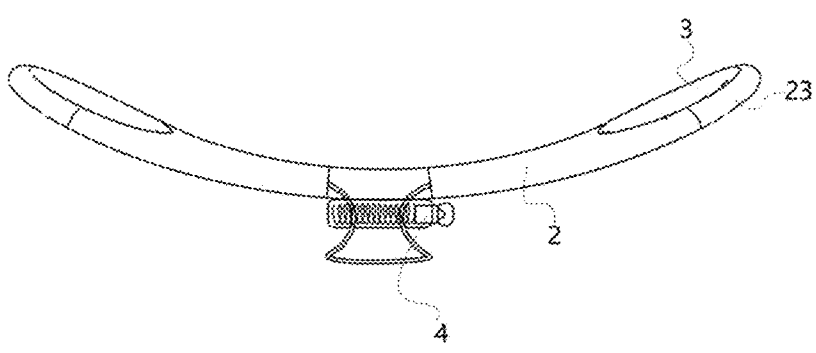
FIG. 19 is a schematic view of the nasal dilator device according to an embodiment of the present disclosure, in which the adjusting assembly is implemented as a strap-and-buckle structure.

In one form, the adjusting assembly 4 is a strap-and-buckle structure (as shown in FIG. 19). In this case, the adjusting mechanism 41 includes a fixing component with a one-way sliding snap, and the tensioning member 42 is a cord structure. During adjustment, the patient threads the tensioning member 42 through the snap and pulls it in a single direction, allowing the tensioning member 42 to be gradually tightened, and upon release, the snap automatically locks. If it is necessary to loosen the tensioning member 42, pressing the unlocking member allows reverse release. This structure provides the advantages of rapid adjustment operation, high adaptability, a wide adjustment range, and is particularly suitable for lightweight design.

Figure 31:
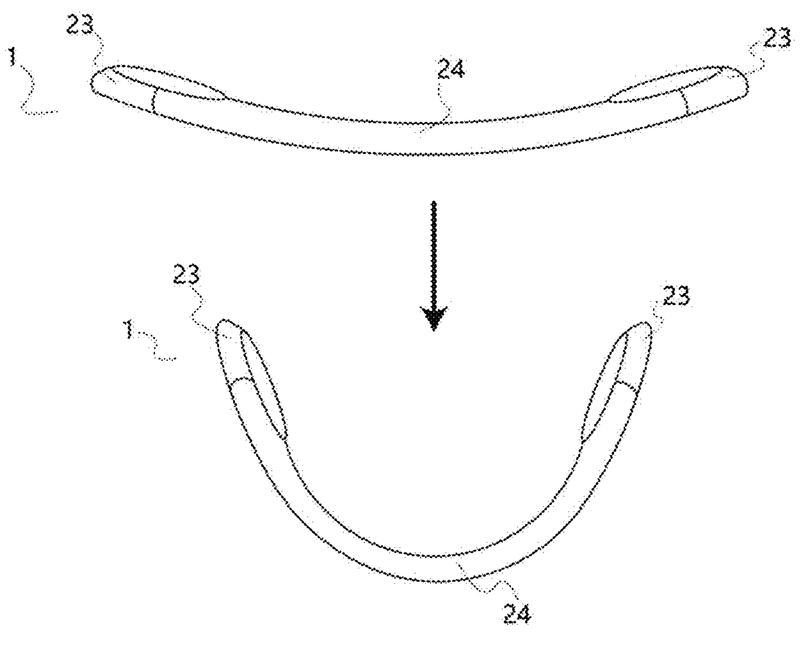
FIG. 31 is a schematic view of an elastic tension-type structure in an embodiment of the present disclosure.

In one form, the adjusting assembly 4 is an elastic tension-type structure, in which the adjusting mechanism 41 omits complex mechanical components and directly uses a stretchable material. During use, the patient can create an automatically adaptive tension by stretching this component, and the elastic member can automatically adjust and maintain appropriate fastening force as the wearing position or facial curvature changes. For example, the adjusting assembly 4 can be a malleable metal sheet disposed within the body of the supporting member 2 (such as aluminum-manganese alloy, copper-aluminum alloy strip, or the like), in which case both the adjusting mechanism 41 and the tensioning member 42 are the metal sheet itself (as shown in FIG. 31), with a cross-sectional size of 0.5 mm to 10 mm in width and 0.2 mm to 5 mm in thickness. The patient can manually bend the supporting member 2, causing the left and right ends to open outward to the desired expansion angle, and the bent shape can be maintained to provide stable expansion force. This structure provides high wearing comfort, simple operation, and strong automatic adaptation capability. To enhance adjustment precision and wearing comfort, a flexible covering layer, such as silicone, thermoplastic elastomer (TPE), or skin-friendly polyurethane coating, can be applied externally to the structure to avoid irritation or pressure on the skin from exposed metal or rack structures.

Figure 23:
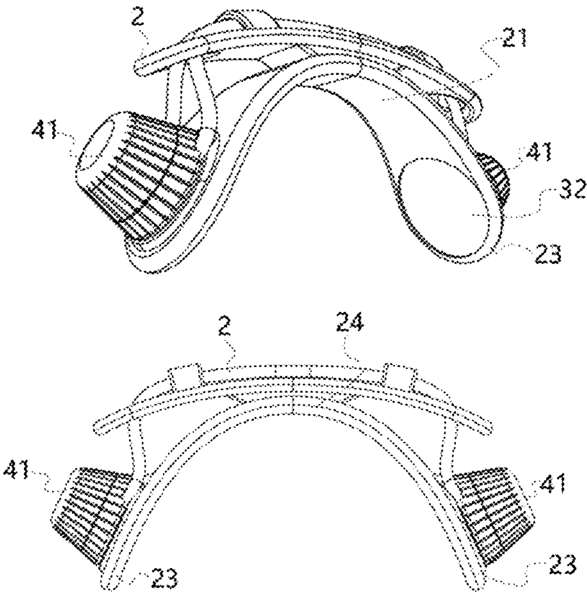
FIG. 23 is a schematic view of a nasal dilator device with multiple adjustment assemblies in an embodiment of the present disclosure.

In some implementations, the adjusting assembly 4 includes multiple assemblies. In one case, the adjusting assemblies 4 are configured to allow segmented adjustment at the patient's left and right nasal wing regions, the middle nasal bridge region, and the peripheral extension regions. For example, the expansion angles of the left and right sides can be individually adjusted, while fine bending control can be applied to the central region to accommodate different nasal shapes, varying degrees of nasal collapse, or changes in airway resistance. The adjusting assemblies can cooperatively control overall tension or individually adjust each point's angle to achieve flexible, distributed expansion. In one case, the nasal dilator device 1 includes two adjusting assemblies 4, respectively disposed at the left and right end portions 23 of the supporting member 2 (as shown in FIG. 23). Each adjusting assembly 4 includes an independent adjusting mechanism 41. The two adjusting mechanisms 41 control the expansion angles of the two end portions 23 through separate cord structures, allowing the patient to adjust each side according to the actual morphology of the left and right nasal wings. For example, if the left nasal wing requires stronger support and the right side is relatively wide, the adjustment of the left adjusting mechanism 41 can be increased to tighten the corresponding cord structure and increase the expansion angle, while the right adjusting mechanism 41 is only lightly tightened to provide a smaller outward force. This structure is particularly suitable for cases with asymmetric nasal wings, differences in cartilage support, or varied airway patency, allowing the patient to flexibly control the expansion state on each side to improve comfort and functional efficiency. In other implementations, the nasal dilator device 1 is further extended to include four adjusting assemblies 4. In addition to having a knob-type adjusting assembly at each of the left and right end portions 23, two auxiliary adjusting assemblies are additionally disposed near the lateral regions adjacent to the end portions 23, forming a four-point adjustable structure. This configuration allows the entire supporting member 2 to achieve a more complex and precise deformation path, enabling not only overall opening angle adjustment but also local tension distribution control.

To ensure a stable connection between the supporting member 2 and the fitting assembly 3, a fixing structure 5 is also provided. The fixing structure 5 is at least disposed at the left and right ends of the supporting member 2, and the adjusting assembly 4 engages with the supporting member 2 through the fixing structure 5. In some cases, the fixing structure 5 is additionally disposed at intermediate portions of the left and right ends of the supporting member 2. The fixing structure 5 includes a structure connected to the tensioning member 42 and a structure connected to the adjusting mechanism 41. The fixing structure can take various forms, such as a hole-type, snap-type, slot-type, rotating shaft-type, sliding groove-type, or nested structure. The fixing structure 5 can be integrally formed with the supporting member 2, or the fixing structure 5 and the supporting member 2 can be separate components joined during use through at least one physical or chemical connection.

In some implementations, the middle section 24 of the supporting member 2 is configured with a serrated structure (as shown in FIGS. 17A and 17B). The serrated structure is continuously arranged along the length direction of the middle section 24, forming multiple alternating bend angles, which can be acute, right, or obtuse angles, so that the middle section 24 has a compliant structural form capable of better deforming under external forces. The serrated structure is realized through local thinning or geometric shape design, allowing the middle section 24 to flexibly bend and adjust its shape under applied force, thereby enabling the supporting member 2 to better conform to the patient's nasal curvature and improving wearing comfort and stability. Furthermore, the serrated structure effectively disperses and cushions pressure at the nasal bridge, reducing localized compression caused by a rigid supporting member 2 and decreasing patient discomfort. The size, depth, and angle of the serrations can be adjusted according to different application requirements, with a thickness generally controlled between 0.1 mm and 5 mm to balance sufficient support strength and good flexibility. Through this serrated design, the middle section 24 of the supporting member 2 achieves structural compliance while enhancing protection of the nasal bridge area, meeting the wearing requirements of users with different nasal shapes. This structure is particularly suitable for supporting members 2 made of semi-rigid materials, thermoplastic elastomers, or shape-memory polymers, allowing the supporting member 2 to maintain necessary expansion force while flexibly adjusting its shape to adapt to diverse nasal contours. The serrated design also facilitates manufacturing through processes such as laser cutting, die-cutting, or stamping, ensuring production efficiency and product consistency. This embodiment provides a nasal dilator solution that is both comfortable and practical by incorporating a serrated structure in the middle section 24 of the supporting member 2.

Embodiment 2

The nasal dilator device 1 of this embodiment includes a supporting member 2 having a first side 21 facing the patient's face during use and a second side 22 opposite the patient's face. The supporting member 2 further has at least two oppositely disposed end portions 23 and is configured to transversely fit against the patient's nose during use. The supporting member 2 is at least partially made of elastic material and has a tendency for its left and right ends to extend downward. A fitting assembly 3 includes at least two first connecting portions 31 that attach to the patient's nose during use and at least two second connecting portions 32 that are at least partially connected to the left and right ends of the supporting member 2, the fitting assembly 3 being configured to interconnect during use. An adjusting assembly 4 includes at least one adjusting mechanism 41 and at least one tensioning member 42, the adjusting assembly 4 being configured to engage with the supporting member 2, and during use, the adjusting mechanism 41 controls the tensioning member 42 to adjust the angles of the left and right ends of the supporting member 2. The adjusting assembly 4 is joined to the supporting member 2 via a fixing structure 5, which is at least disposed at the left and right ends of the supporting member 2. The adjusting mechanism 41 is configured for incremental adjustment and can be fixed after adjustment; for example, a ratchet structure allows rotation in only one direction when the ratchet is not released to achieve fixation, or in a drawstring-type structure, the end or a portion of the drawstring is secured at a fixed point after adjustment to prevent movement. The adjusting mechanism 41 includes at least a first mechanism configured to tension the tensioning member 42 and a second mechanism configured to relax the tensioning member 42. The operation of the adjusting assembly 4 is such that applying a force to the adjusting mechanism 41 drives the tensioning member 42, transmitting force to the left and right ends 23 of the supporting member 2, thereby raising at least portions of the left and right ends toward the second side 22. The length of the tensioning member 42 is greater than its width.

The difference between this embodiment and Embodiment 1 lies in that at least one portion of the supporting member 2 is connected to a comfort layer, as shown in FIGS. 27A, 27B and 27C. In this embodiment, the connection location can be positioned at the middle, at either end, or at any other area where increased fit and comfort are desired to accommodate different users' needs. The comfort layer may be made of one or more of the following materials: silicone, cotton, fabric, gel, or thermoplastic elastomer. These materials provide good cushioning, effectively reducing pressure, friction, or allergy risks on the skin during use. Additionally, the comfort layer may have features such as breathability, anti-slip properties, and moisture-wicking to further enhance wearing comfort. The comfort layer can be integrally connected with the supporting member 2 or detachably connected. The detachable connection allows the comfort layer to be reused and facilitates cleaning.

The nasal dilator device 1 of this disclosure provides at least the following beneficial effects:

1. The adjustable nasal dilator device 1 of this disclosure represents a pioneering device in the current market with autonomous adjustment functionality, filling the technological gap of existing products in the field of adjustable nasal dilators. The device employs innovative structural design and adjusting mechanisms, overcoming long-standing technical limitations of conventional nasal dilator devices in terms of adaptability, comfort, and adjustment flexibility, and achieves personalized expansion effects for different nasal anatomies and individual needs. Conventional nasal dilator devices on the market mainly include disposable patch-type devices and integrated nasal expansion devices, with the integrated nasal patch structure being the most common. While these devices can improve nasal ventilation to some extent, they generally rely on a single mechanical stretching method, resulting in limited expansion effects and insufficient adaptability to diverse patient needs under different usage scenarios. Moreover, integrated fitting assemblies tend to experience reduced adhesiveness, detachment, or cause skin discomfort during long-term use, resulting in insufficient wearing comfort and durability. The market has introduced detachable or structurally simplified nasal dilator devices, such as magnetic-based products, which use modular or split designs to improve convenience and reusability. However, such devices still present deficiencies in safety, material biocompatibility, cost control, and manufacturing complexity. For example, magnetic components may pose risks in terms of attraction strength and stability, some materials may cause skin or mucosal discomfort, and multi-component designs increase manufacturing costs and operational complexity. In contrast, the disclosure described herein allows the expansion force and angles to be freely adjusted according to individual nasal anatomy. This design enhances wearing comfort and structural stability while ensuring durability and safety. The modular and adjustable structure enables adaptation to a broader patient population and meets long-term usage requirements, providing advantages over conventional devices in terms of safety, comfort, durability, and cost-effectiveness, and demonstrating significant innovation and practical value.
2. Specifically, with respect to adaptability and flexibility, the adjustable nasal dilator device 1 of this disclosure includes adjusting assembly 4 that allows precise modulation according to the patient's nasal anatomy, nasal wing width, and individual usage habits. The device enables patients to adjust both the magnitude and angles of the expansion force in different usage scenarios, achieving a highly accurate fit and significantly improving nasal ventilation efficiency and breathing smoothness. Patients may encounter various conditions in daily life, including changes in sleep posture, differences in environmental humidity and temperature, variations in respiratory states at different times, and minor physiological changes in the nasal cavity, all of which affect nasal ventilation requirements. The adjustable nasal dilator device 1 addresses these diverse needs, allowing patients to obtain a personalized and comfortable experience with stable expansion effects without the need to frequently replace devices of different sizes or specifications. Furthermore, the adjustable functionality reduces interruptions due to discomfort or improper fit, enhances long-term compliance, and improves overall quality of life, thereby providing comprehensive support for respiratory health while balancing flexibility, comfort, and effectiveness.
3. With respect to performance, the adjustable nasal dilator device 1 of this disclosure provides multiple additional advantages. First, in other adjustable devices available in the market, insufficient design of the adjusting mechanism often leads to rebound, deformation, or displacement during use, resulting in ineffective expansion or instability. To address this, the disclosure introduces an innovative integrated adjustment-and-locking mechanism, which allows angle adjustments to be performed flexibly while maintaining the preset position stably without requiring additional tools or auxiliary components. This mechanism resolves the conventional technical contradiction between "adjustable but unstable" and "stable but non-adjustable." Moreover, it ensures continuous output of expansion force and stability of the target effect, maintaining reliable fit and effective dilation even during sleep, changes in body posture, or daytime activities. The design also facilitates operation, enabling patients to quickly complete angle adjustment and position locking, enhancing usability and adaptability to diverse nasal anatomies and individual needs. Second, in one embodiment of the present disclosure, the adjusting assembly 4 includes a knob structure and a tensioning member 42, with the adjusting mechanism 41 in the form of a knob. In this configuration, patients can easily drive the tensioning member 42 by rotating or pushing the knob, applying balanced tension to the two end portions 23 of the supporting member 2 to achieve precise expansion of the nasal wings. This adjustment approach is simple and convenient, allowing patients to perform rapid adjustments and greatly improving operational portability. It lowers the usage threshold, reduces the risk of misuse, and is particularly suitable for elderly patients, children, or individuals with limited hand dexterity. In addition, the adjusting assembly 4 of this disclosure provides superior expansion performance compared to adjusting mechanisms available in the market. Compared to conventional market devices that rely primarily on pre-set elastic materials for expansion, the adjusting assembly 4 of this disclosure enables more precise modulation of the two ends of the supporting member 2 with less applied force. During use, the force remains balanced and stable, significantly improving the expansion range and consistency. Third, In this adjusting mechanism 41, the adjusting mechanism 41 and the tensioning member 42 work cooperatively, allowing simple operations to simultaneously adjust both end portions 23 of the supporting member 2, ensuring uniform tension distribution across both sides of the nose, reducing local pressure or discomfort, and improving patient wearing comfort.

4. Additionally, the nasal dilator device 1 of the present disclosure provides the advantage of a reusable design. Many nasal dilator devices available in the current market are primarily designed for single-use or lack the capability for repeated adjustment. While such devices are simpler to manufacture, their limited usage cycle prevents repeated adjustment, and long-term use may negatively affect wearing comfort and overall user experience, making it difficult to meet patient demands for durability and personalized adaptation. In contrast, the disclosure described herein allows patients to avoid frequently replacing single-use products, significantly reducing usage and treatment costs. Moreover, the reusable nature of the device effectively minimizes waste generation, alleviates environmental impact, and aligns with principles of green and sustainable development.
5. In the present disclosure, the supporting member 2 made of elastic material is configured to conform to the patient's skin during use. This material not only maintains the set shape after adjustment, preventing loss of expansion force due to rebound, but also ensures lightweight, low skin irritation, and long-term contact safety, allowing the patient to maintain comfort during extended use. In conventional nasal dilator devices, material selection often presents significant limitations: purely rigid materials can provide the necessary support but lack flexibility, potentially causing localized pressure and reducing wearing comfort; fully flexible materials, while soft and comfortable, are unable to provide sufficient expansion force and may lack stability over long-term use, leading to deformation or failure. To address these issues, this disclosure overcomes the limitations of purely rigid or flexible materials, optimizing the material properties to achieve a balance between functionality, stability, and comfort. In one embodiment, a composite material strategy is employed, allowing the nasal dilator device 1 to be more suitable for use and to work in coordination with the adjusting mechanism 41, thereby providing significant innovation and practical value.

The technical characteristics described in the above embodiments of the present disclosure may be combined in any suitable manner. For the sake of brevity, not all possible combinations of the technical features in the foregoing embodiments have been described in detail; however, as long as such combinations do not result in contradictions, they shall be considered as falling within the scope of the present disclosure.

The embodiments described above represent only several implementations of the present disclosure, which are provided in a specific and detailed manner for illustrative purposes, and should not be construed as limiting the scope of protection of the present disclosure. It should be noted that those of ordinary skill in the art, without departing from the concept and spirit of the present disclosure, may make various modifications and improvements, all of which shall fall within the protection scope of the present disclosure. Therefore, the protection scope of the present disclosure shall be defined by the appended claims.

It must be noted that as used herein and in the appended claims, the singular forms "a", "an", and "the" include their plural equivalents, unless the context clearly dictates otherwise.

The invention claimed is:

1. An adjustable nasal dilator device, configured to conform to a patient's nose and apply expansion force to a nasal cavity region to enhance the patient's breathing capacity through a nasal airway, the device comprising:

a supporting member comprising a first side facing the patient's face and a second side opposite the patient's face during use, the supporting member further having at least two end portions arranged opposite to each other and configured to laterally conform to the patient's nasal sides during use;

wherein the supporting member has a tendency for left and right ends of the supporting member configured to extend downward;

a fitting assembly comprising at least two first connecting portions configured to attach to the patient's nose during use, and at least two second connecting portions at least partially connected to the left and right ends of the supporting member, the fitting assembly is configured to mutually engage during use; and an adjusting assembly comprising at least one adjusting mechanism and at least one tensioning member, the adjusting assembly configured to engage with the supporting member and, during use, adjust an angle of the left and right ends of the supporting member via the at least one tensioning member controlled by the at least one adjusting mechanism;

wherein the adjusting assembly engages with the supporting member via a fixing structure, the fixing structure is at least provided at the left and right ends of the supporting member; and wherein the at least one adjusting mechanism is configured for incremental adjustment.

2. The nasal dilator device according to claim 1, wherein the supporting member is at least partially made of an elastic material.

3. The nasal dilator device according to claim 1, wherein the at least one adjusting mechanism comprises at least a first mechanism configured to tension the at least one tensioning member and a second mechanism configured to release the at least one tensioning member.

4. The nasal dilator device according to claim 3, wherein the first mechanism is configured to apply force in a first direction to tension the at least one tensioning member, and the second mechanism is configured to apply force in a second direction to release the at least one tensioning member.

5. The nasal dilator device according to claim 4, wherein the first direction and the second direction are perpendicular to each other.

6. The nasal dilator device according to claim 4, wherein the first direction and the second direction are completely opposite or at least partially opposite.

7. An adjustable nasal dilator device, configured to conform to a patient's nose and apply expansion force to a nasal cavity region to enhance the patient's breathing capacity through a nasal airway, the device comprising:

a supporting member comprising a first side facing the patient's face during use and a second side opposite the patient's face, the supporting member further having at least two end portions arranged opposite to each other and configured to laterally conform to the patient's nasal sides during use;

wherein the supporting member has a tendency for left and right ends of the supporting member configured to extend downward;

a fitting assembly comprising at least two first connecting portions configured to attach to the patient's nose during use, and at least two second connecting portions at least partially connected to the left and right ends of the supporting member, the fitting assembly is configured to mutually engage during use; and an adjusting assembly comprising at least one adjusting mechanism and at least one tensioning member, the adjusting assembly configured to engage with the supporting member and, during use, adjust an angle of the left and right ends of the supporting member via the at least one tensioning member controlled by the at least one adjusting mechanism;

wherein the adjusting assembly engages with the supporting member via a fixing structure, the fixing structure is at least provided at the left and right ends of the supporting member; and wherein the at least one adjusting mechanism is configured to be fixed after adjustment.

8. The nasal dilator device according to claim 7, wherein the supporting member is at least partially made of an elastic material.

9. The nasal dilator device according to claim 7, wherein the at least one adjusting mechanism is a knob structure.

10. The nasal dilator device according to claim 9, wherein the at least one adjusting mechanism comprises at least a ratchet wheel, a housing, a fastening member, a rotary disc, and a bottom member.

11. The nasal dilator device according to claim 10, wherein the at least one adjusting mechanism is configured such that the ratchet wheel is coupled with the housing, the fastening member and the rotary disc are integrated, and the housing is connected to the bottom member.

12. The nasal dilator device according to claim 9, wherein the at least one tensioning member is arranged in parallel within the at least one adjusting mechanism.

13. The nasal dilator device according to claim 9, wherein the at least one tensioning member is arranged in a crossed configuration within the at least one adjusting mechanism.

14. An adjustable nasal dilator device, configured to conform to a patient's nose and apply expansion force to a nasal cavity region to enhance the patient's breathing capacity through a nasal airway, the device comprising:

a supporting member comprising a first side facing the patient's face during use and a second side opposite the patient's face, the supporting member further having at least two end portions arranged opposite to each other and configured to laterally conform to the patient's nasal sides during use;

wherein the supporting member has a tendency for left and right ends of the supporting member configured to extend downward;

a fitting assembly comprising at least two first connecting portions configured to attach to the patient's nose during use, and at least two second connecting portions at least partially connected to the left and right ends of the supporting member, the fitting assembly is configured to mutually engage during use; and an adjusting assembly comprising at least one adjusting mechanism and at least one tensioning member, the adjusting assembly configured to engage with the supporting member and, during use, adjust an angle of the left and right ends of the supporting member via the at least one tensioning member controlled by the at least one adjusting mechanism;

wherein the at least one adjusting mechanism comprises at least a first mechanism configured to tension the at least one tensioning member and a second mechanism configured to release the at least one tensioning member; and wherein the adjusting assembly engages with the supporting member via a fixing structure, the fixing structure is at least provided at the left and right ends of the supporting member.

15. The nasal dilator device according to claim 14, wherein the supporting member is at least partially made of an elastic material.

16. The nasal dilator device according to claim 14, wherein the fixing structure is further provided at a middle portion of the left and right ends of the supporting member.

17. The nasal dilator device according to claim 14, wherein the fixing structure is integrally formed with the supporting member.

18. The nasal dilator device according to claim 14, wherein the fixing structure and the supporting member are two separate components, which are engaged during use via at least one of a physical connection or a chemical connection.

19. An adjustable nasal dilator device, configured to conform to a patient's nose and apply expansion force to a nasal cavity region to enhance the patient's breathing capacity through a nasal airway, the device comprising:

a supporting member comprising a first side facing the patient's face during use and a second side opposite the patient's face, the supporting member further having at least two end portions arranged opposite to each other and configured to laterally conform to the patient's nasal sides during use;

wherein the supporting member is at least partially made of an elastic material and is configured to have a tendency for left and right ends of the supporting member to extend downward;

a fitting assembly comprising at least two first connecting portions configured to attach to the patient's nose during use, and at least two second connecting portions at least partially connected to the left and right ends of the supporting member, the fitting assembly is configured to mutually engage during use; and an adjusting assembly comprising at least one adjusting mechanism and at least one tensioning member, the adjusting assembly configured to engage with the supporting member and, during use, adjust an angle of the left and right ends of the supporting member via the at least one tensioning member controlled by the at least one adjusting mechanism;

wherein the adjusting assembly is configured such that a force applied to the at least one adjusting mechanism drives the at least one tensioning member and transmits the force to the left and right ends of the supporting member, thereby causing at least a portion of the left and right ends to lift toward the second side;

wherein the at least one tensioning member has a length greater than its width.

20. The nasal dilator device according to claim 19, wherein the supporting member further comprises a middle section connecting the at least two end portions.

21. The nasal dilator device according to claim 20, wherein the middle section and the at least two end portions are integrally formed.

22. The nasal dilator device according to claim 20, wherein the middle section structure and the at least two end portions are two separate components.

23. The nasal dilator device according to claim 19, wherein a thickness of the supporting member ranges from 0.1 mm to 20 mm.

24. The nasal dilator device according to claim 19, wherein the fitting assembly is engaged with the supporting member by at least one of a snap-fit connection, adhesive connection, magnetic connection, threaded connection, or hook-and-loop connection.

* * * * *